United States Patent [19]

Habibi

[11] Patent Number: 5,760,000

[45] Date of Patent: Jun. 2, 1998

[54] INHIBITION OF LIVER CANCER BY THE USE OF GNRH AND GNRH ANALOGS

[75] Inventor: Hamid R. Habibi, Calgary, Canada

[73] Assignee: University Technologies International, Inc., Calgary, Canada

[21] Appl. No.: 242,678

[22] Filed: May 13, 1994

[51] Int. Cl.$^6$ .............................. A61K 38/09; C07K 7/23; C12Q 1/04; G01N 33/574

[52] U.S. Cl. ................... 514/15; 435/7.23; 435/34; 436/64; 436/813; 530/313; 930/130

[58] Field of Search ..................... 530/313; 930/130; 514/15; 435/7.23, 34, 35; 436/64, 813

[56] References Cited

U.S. PATENT DOCUMENTS

| | | | |
|---|---|---|---|
| 4,410,514 | 10/1983 | Vale, Jr. et al. | 514/15 |
| 4,760,053 | 7/1988 | Labrie | 514/15 |
| 4,820,641 | 4/1989 | Nakanishi et al. | 530/388.8 |
| 5,091,367 | 2/1992 | Konig et al. | 514/15 |
| 5,378,688 | 1/1995 | Nett et al. | 514/15 |
| 5,411,943 | 5/1995 | Bogden | 514/15 |

FOREIGN PATENT DOCUMENTS

| | | |
|---|---|---|
| 2218335 | 11/1989 | United Kingdom . |
| WO 91/16343 | 10/1991 | WIPO . |
| WO 92/12247 | 7/1992 | WIPO . |

OTHER PUBLICATIONS

Bogerd et al, Two Gonadotropin–Releasing Hormones From African Catfish. Biochem. Biophys. Res. Comm. 1992, vol. 187, No. 1, pp. 127–134.

Sherwood et al, Characterization of a teleost gonadotropin–releasing hormone. PNAS. May 1983, vol. 80, pp. 2794–2798.

American Chemical Society, 200th ACS National Meeting, Abstracts of Papers Part 1, issued 1990, Gombotz et al, "The Use of Controlled Release Devices In Commercial", Abstract AGRO 17.

Endocrinology, vol. 132, No. 3, issued 1993, Sower et al, "Primary Structure and Biological Activity of a . . . ", pp. 1125–1131.

Eur. J. Clin. Oncol., vol. 25, No. 9, issued 1989, Falkson et al, "Phase II Trial of Buserelin in Hepatocellular Carcinoma", pp. 1339–1340.

The Merck Index, 11th ed., published 1989 by Mercke Co., Inc. (Rahway), p. 229.

Lindhe et al., "Effects of Neonatal and Adult Castration and of Testosterone Substitution in Male Rats on Growth and Enzyme–altered Hepatic Foci in the Resistant Hepatocyte Model", Cancer Research 50: 2679–2682 (1990).

International Search Report, PCT IB95/00323, issued 28 Jul. 1995.

Eidne, Karin A., et al., "Gonadotropin–Releasing Hormone Binding Sites in Human Breast Carcinoma", Science 229: 989–991 (1995).

Forbes, Alastair, et al., "Response to Cyproterone Acetate Treatment in Primary Hepatocellular Carcinoma is Related to Fall in Free 5α–Dihydrotestosterone", Eur J Cancer Clin Oncol 23(11):1659–64 (1987).

(List continued on next page.)

Primary Examiner—Jeffrey E. Russel
Attorney, Agent, or Firm—Burns, Doane, Swecker & Mathis, L.L.P.

[57] ABSTRACT

The invention provides a method for treating liver cancer in a mammal comprising administering to the mammal an inhibitory effective amount of at least one GnRH-related compound. Pharmaceutical preparations useful for the treatment of liver cancer comprising an inhibitory effective amount of at least one GnRH-related compound and a pharmaceutically acceptable carrier are also provided. A further aspect of the invention provides a method for diagnosing liver cancer by determining the presence of receptors for GnRH on a biological sample.

29 Claims, 8 Drawing Sheets

OTHER PUBLICATIONS

Guechot, Jerome, et al., "Effect of D-Tryptophan-6-Luteinizing Hormone-Releasing Hormone on the Tumoral Growth and Plasma Sex Steroid Levels in Cirrhotic Patients with Hepatocellular Carcinoma", Hepatology 10(3):346-8 (1989).

Matsuura, Bunzo, et al., "Effect of antiandrogen treatment on chemical hepatocarcinogenesis in rats", J. Hepatol 21(2), 187-93 (1994).

Miller, W. R., et al., "Growth of human breast cancer cells inhibited by a luteinizing hormone-releasing hormone agonist", 313: 231-33 (1985). Nature.

A. DeLean et al., "Simultaneous analysis of families of sigmoidal curves: application to bioassay, radioligand assay, and physiological dose-response curves," Am. J. Physiol., 235:E97-E102 (1978).

K.A. Eidne et al., "Gonadotropin-Releasing Hormone Binding Sites in Human Breast Carcinoma," Science, 229:989-991 (1985).

M. Fekete et al., "Receptors for Luteinizing Hormone-Releasing Hormone, Somatostatin, Prolactin, and Epidermal Growth Factor in Rat and Human Prostate Cancers and Benign Prostate Hyperplasia," Prostate, 14:191-208 (1989).

H.R. Habibi et al., "Characterization of Gonadotropin-Releasing Hormone (GnRH) Binding to Pituitary Receptors in Goldfish," Biol. Reprod., 36:844-853 (1987).

H.R. Habibi et al., "Extrapituitary gonadotropin-releasing hormone (GnRH) binding sites in goldfish," Fish Physiol. Biochem., 11:43-49 (1993).

H.R. Habibi, et al. "Functional Relationship between Receptor Binding and Biological Activity for Analogs of Mammalian and Salmon Gonadotropin-Releasing Hormones in the Pituitary of Goldfish (*Carassius auratus*)[1]," Biol. Repro. 40:1152-1161 (1989).

H.R. Habibi et al., "Activity of vertebrate gonadotropin-releasing hormones and analogs with variant amino acid residues in positions 5, 7 and 8 in the goldfish pituitary," Regulatory Peptides, 37:271-284 (1992).

H.R. Habibi et al., "GnRH Binding To Human Hepato-Carcinoma Derived Cell Line, HEPG2: Is This An Evolutinary Primitive Feature?," XII Int'l. Congress of Compar. Endocrinol., Toronto A-61 (1993).

D. Heber, et al., "GnRH membrane binding: identification, specificity, and quantification in nonpituitary tissues," Am. J. Phys. 235:E227-E230 (1978).

Mc Pherson, "Analysis of Radioligand Binding Experiments," J. Pharmacol. Methods, 14:213-228 (1985).

R. Millar et al., "Chimeric Analogues of Vertebrate Gonadotropin-releasing Hormones Comprising Substitutions of the Variant Amino Acids in Positions 5, 7, and 8," J. Biol. Chem., 264:21007-21013 (1989).

W. Miller et al., "Growth of human breast cancer cells inhibited by a luteinizing hormone-releasing hormone agonist," Nature, 313:231-233 (1992).

S. Milovanovic et al., "Inhibition of Growth of PC-82 Human Prostate Cancer Line Xenografts in Nude Mice by Bombesin Antagonist RC-3095 or Combination of Agonist [D-Trp[6]]-Luteinizing Hormone-Releasing Hormone and Somatostatin Analog RC-160," The Prostate, 20:269-280 (1992).

Munson et al., "LIGAND: A Versatile, Computerized Approach for Characterization of Ligand-Binding Systems," Anal. Biochem., 107:220-239 (1980).

H. Nakabayashi et al., "Growth of Human Hepatoma Cell Lines with Differentiated Functions in Chemically Defined Medium," Cancer Research 42:3858-3863 (1982).

D. Patel et al., "Metabolism Of A Novel Antitumor Agent, Crisnatol, By A Human Hepatoma Cell Line, Hep G2, and Hepatic Microsomes," Biochem. Pharmacol., 42:337-346 (1991).

D. Pati et al., "Characterization of gonadotropin-releasing hormone receptors in goldfish ovary: variation during follicular development,", Am. J. Physiol., 264:R227-R234 (1993).

T. Redding et al., "Sustained Release Formulations of Luteinizing Hormone-releasing Hormone Antagonist SB-75 Inhibit Proliferation and Enhance Apoptotic Cell Death of Human Prostate Carcinoma (PC-82) in Male Nude Mice[1]," Cancer Research 52:2538-2544 (1992).

T. Reissmann et al., "Treatment of experimental DMBA induced mammary carcinoma with Cetrorelix (SB-75): a potent antagonist of luteinizing hormone-releasing hormone," J Cancer Res. Oncol. 118:44-49 (1992).

A. Schally et al., "Antitumor Effects of Analogs of LH-RH And Somatostatin: Experimental And Clinical Studies," J. Steroid Biochem. Mol. Biol., 37:1061-1067 (1990).

T. Segal-Abramson et al., "Guanine nucleotide modulation of high affinity gonadotropin-releasing hormone receptors in rat mammary tumors," Mol. Cell. Endocrinol., 85:109-116 (1992).

S. Varma, et al. "Human Splenocytes Secrete LHRH, Which Inhibits Lymphocyte Proliferation," Prog. in NeuroEndocrinImmun. 5:187-191 (1992).

Walker et al., "Preliminary endocrinological evaluation of a sustained-release formulation of the LH-releasing hormone agonist D-Ser(BU$^t$)$^6$Azgly$^{10}$LHRH in premenopausal women with advanced breast cancer," J. Endocrinol., 111:349-353 (1986).

T. Yano, et al., "Inhibition of growth of MCF-7 MIII human breast carcinoma in nude mice by treatment with agonists or antagonists of LH-RH," Breast Cancer Research and Treatment, 21:35-45 (1992).

Zar, "Multiple Comparisons," Biostatistical Analysis, Prentice Hall, Inc., New Jersey, Ed. 2, 186-190 (1984).

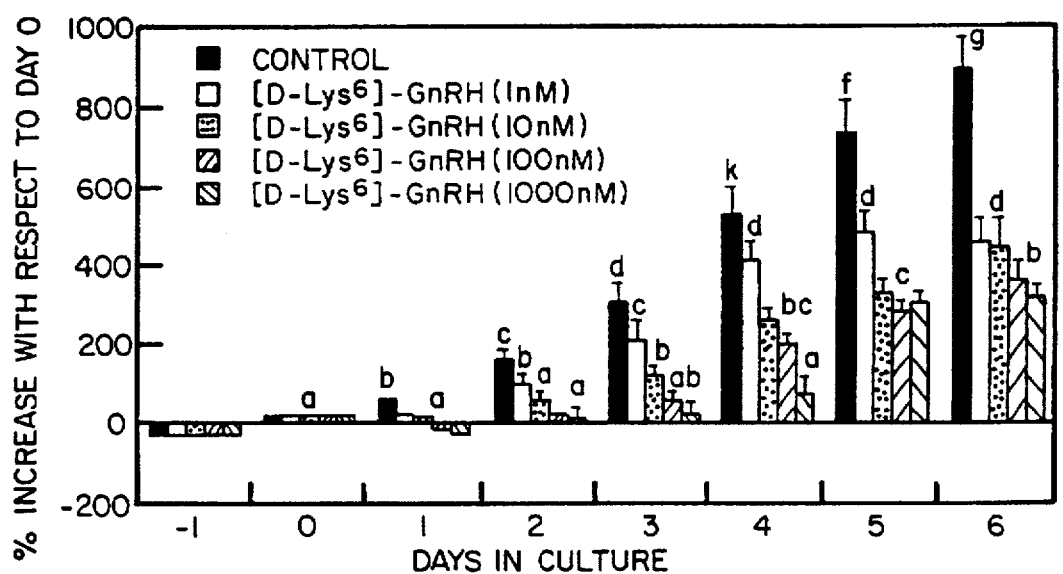
FIG_1A
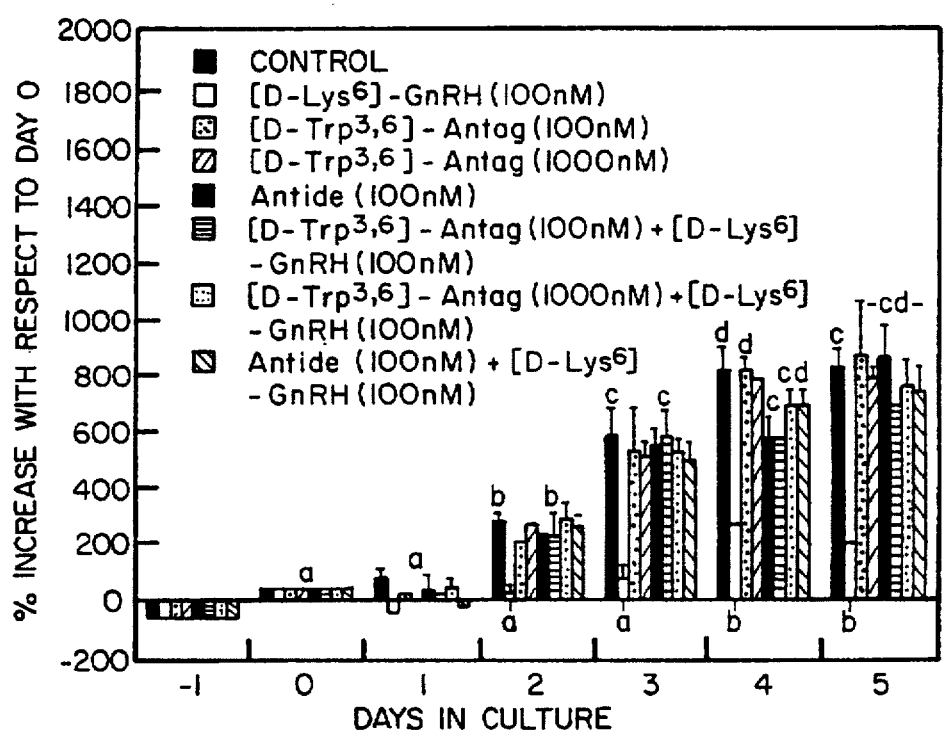
FIG_1B

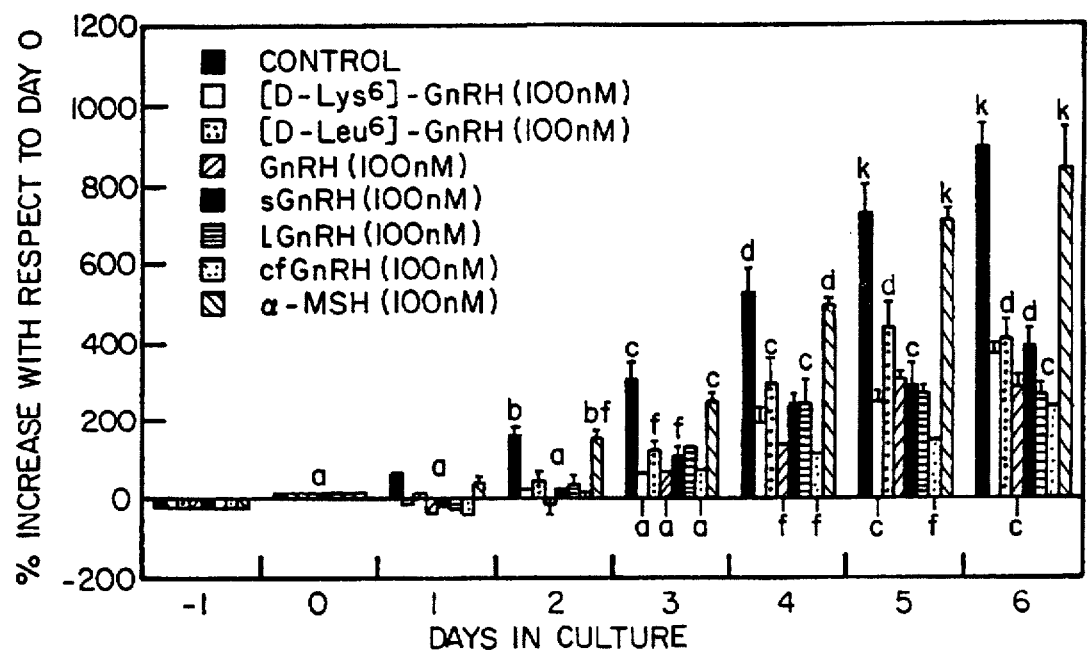
FIG_1C
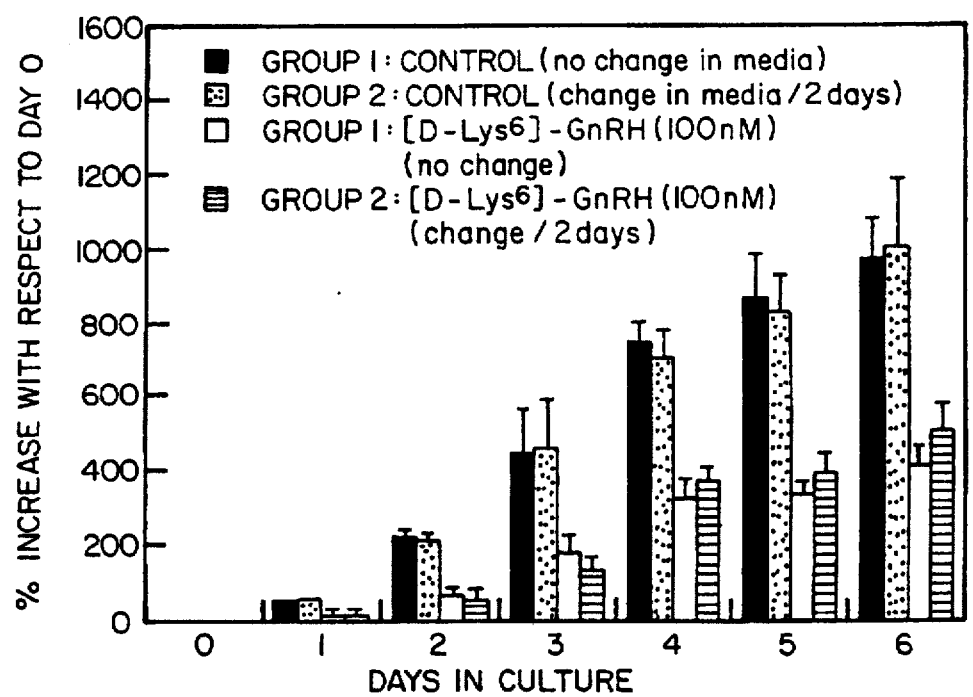
FIG_3

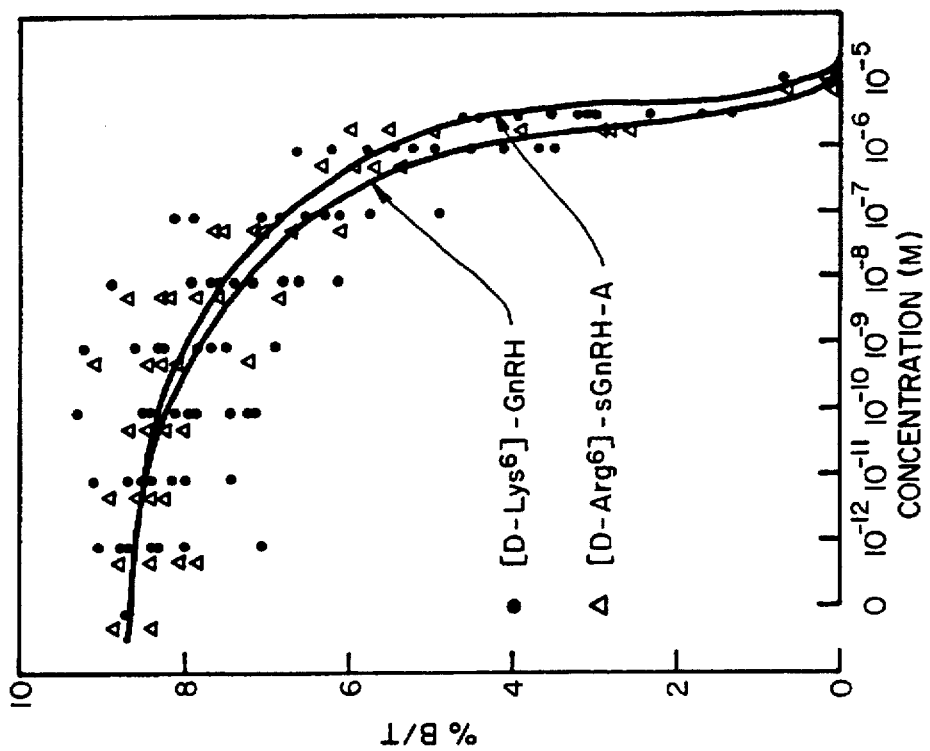
FIG_2C
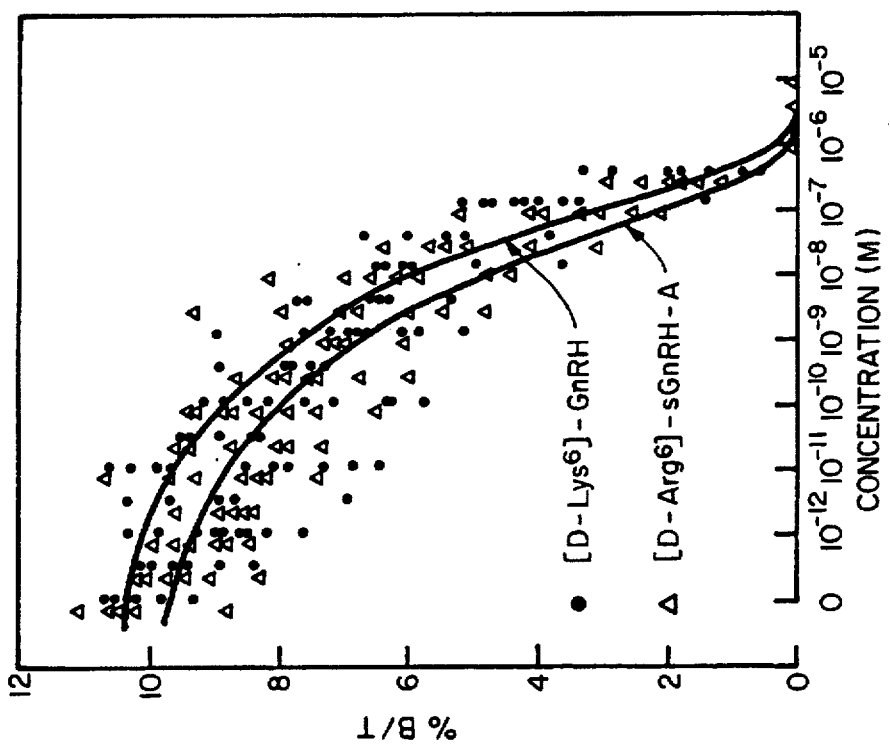
FIG_2A

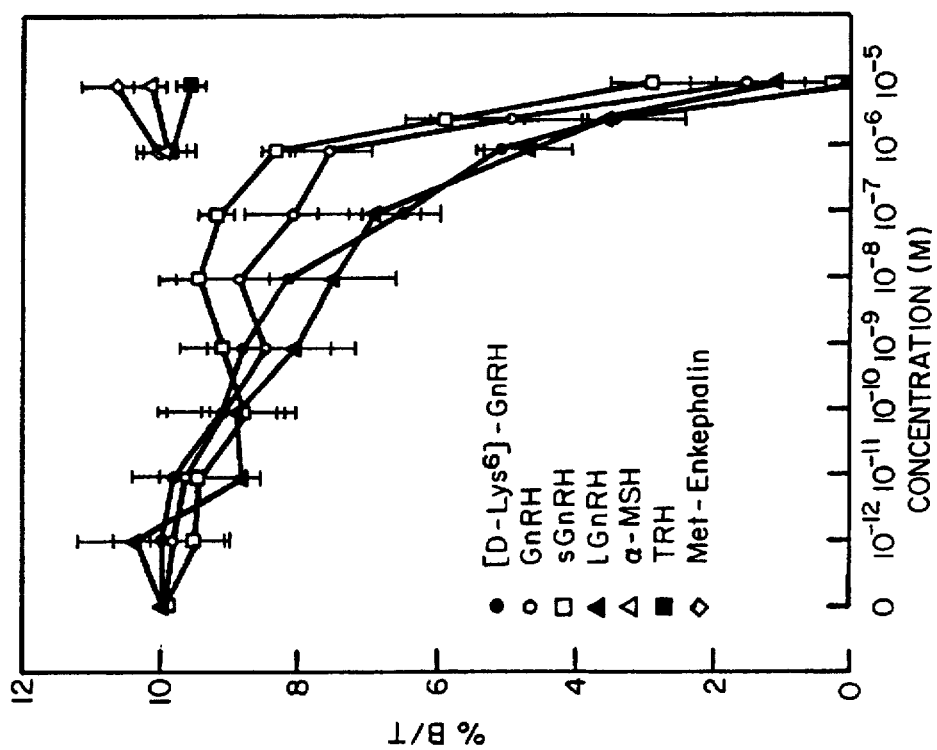
FIG_2D
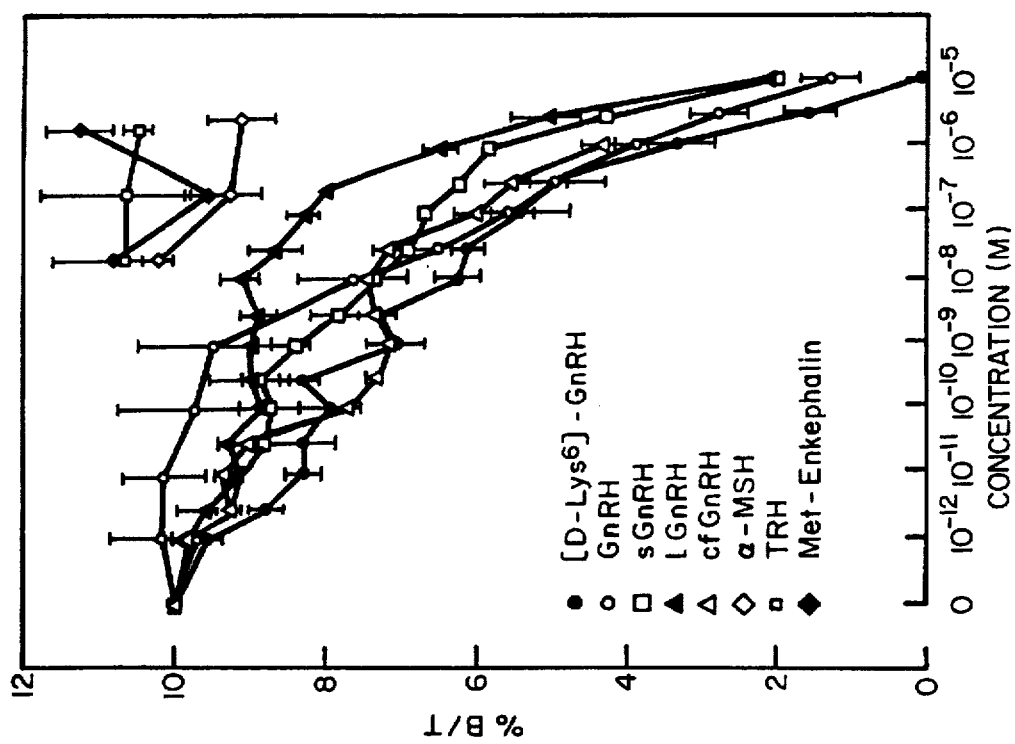
FIG_2B

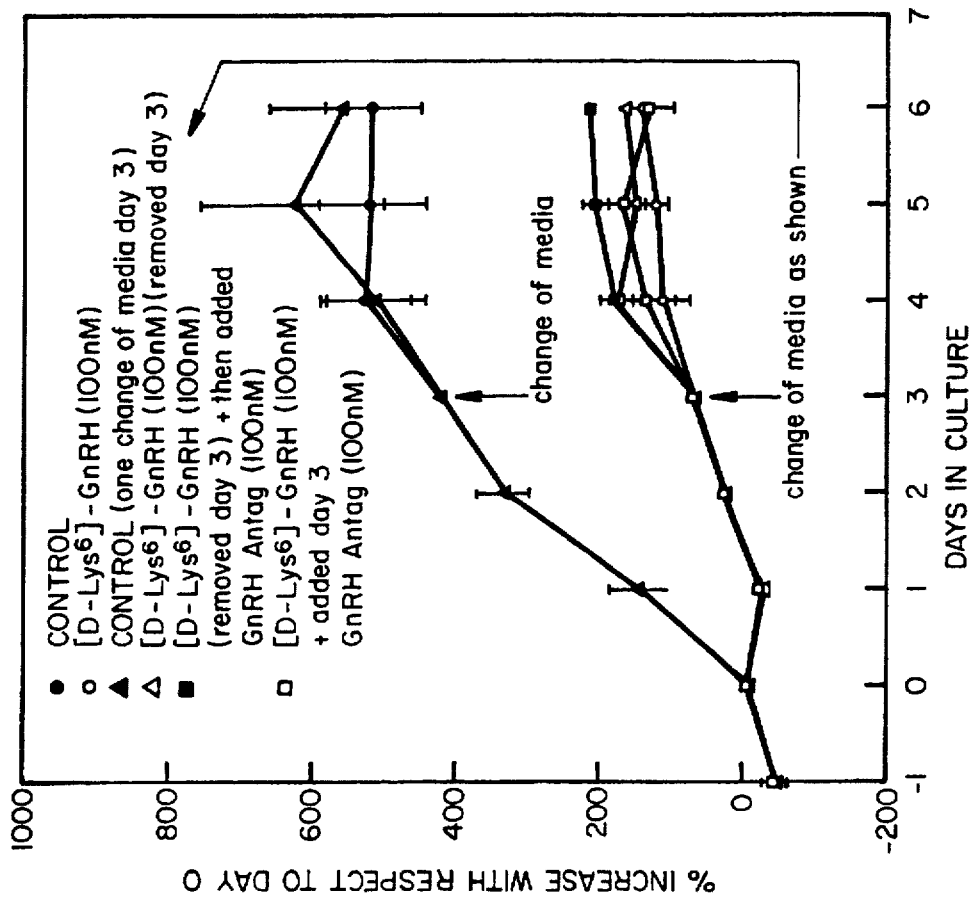
FIG_5
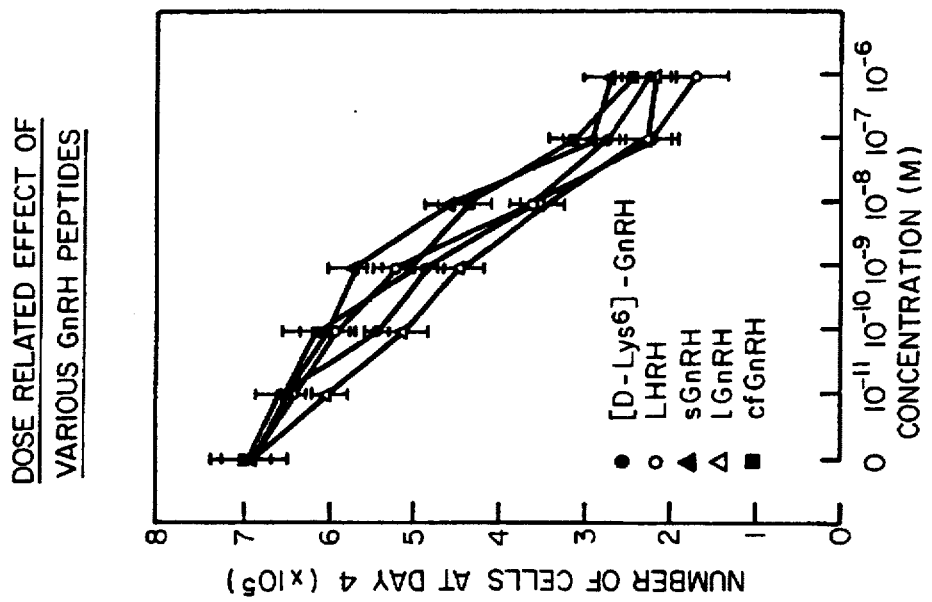
FIG_4

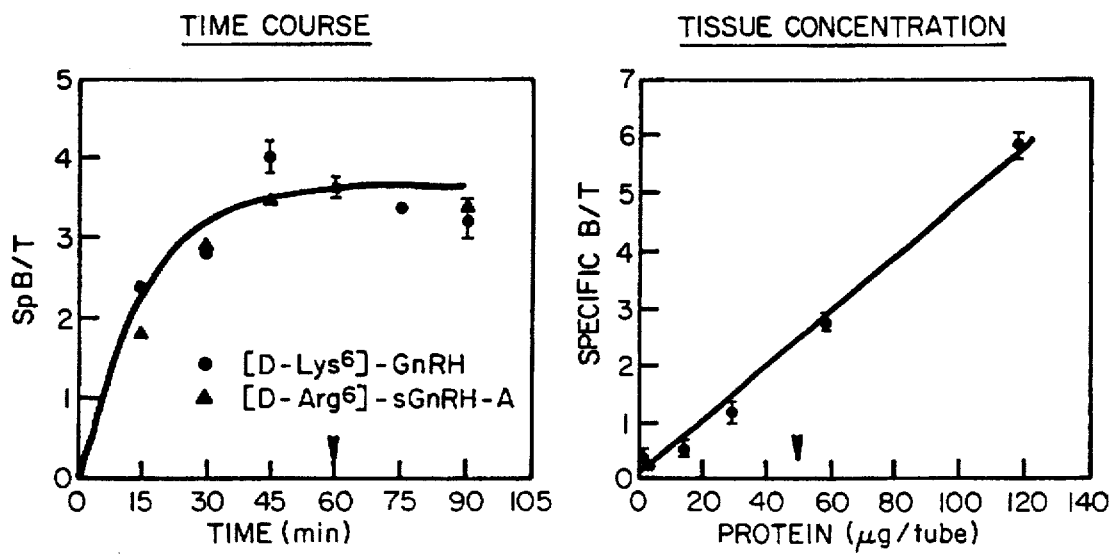
FIG_6A  FIG_6B
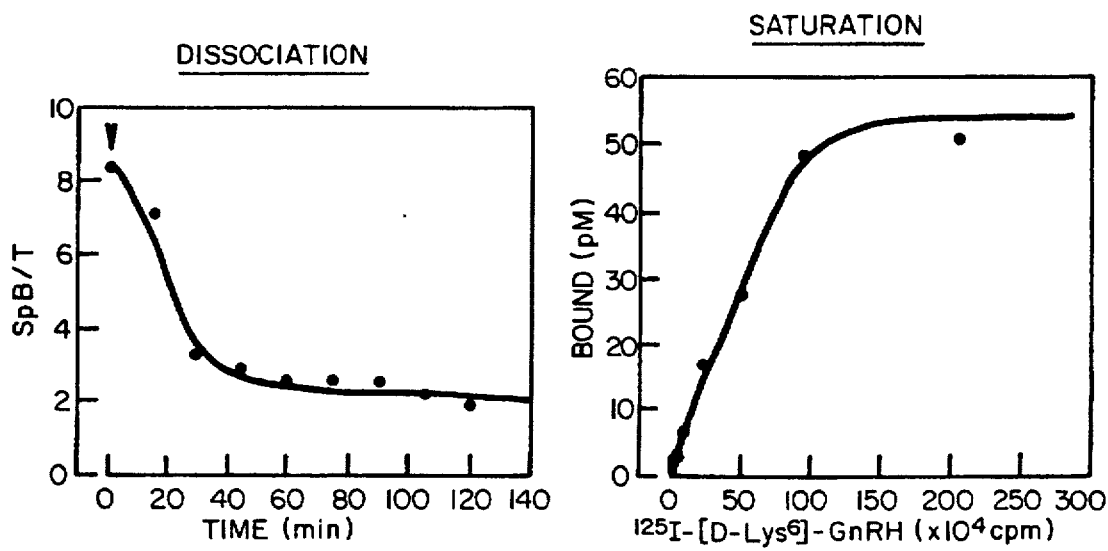
FIG_6C  FIG_6D

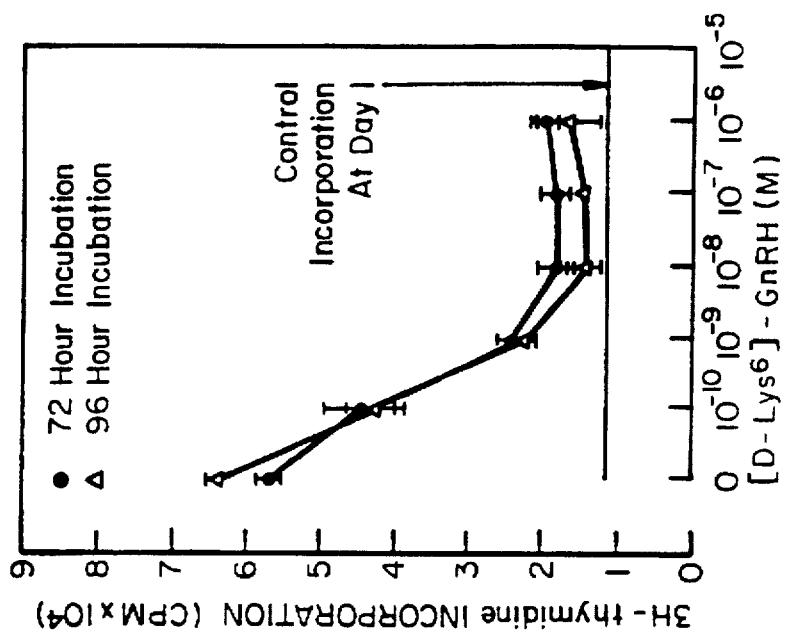
FIG_7B
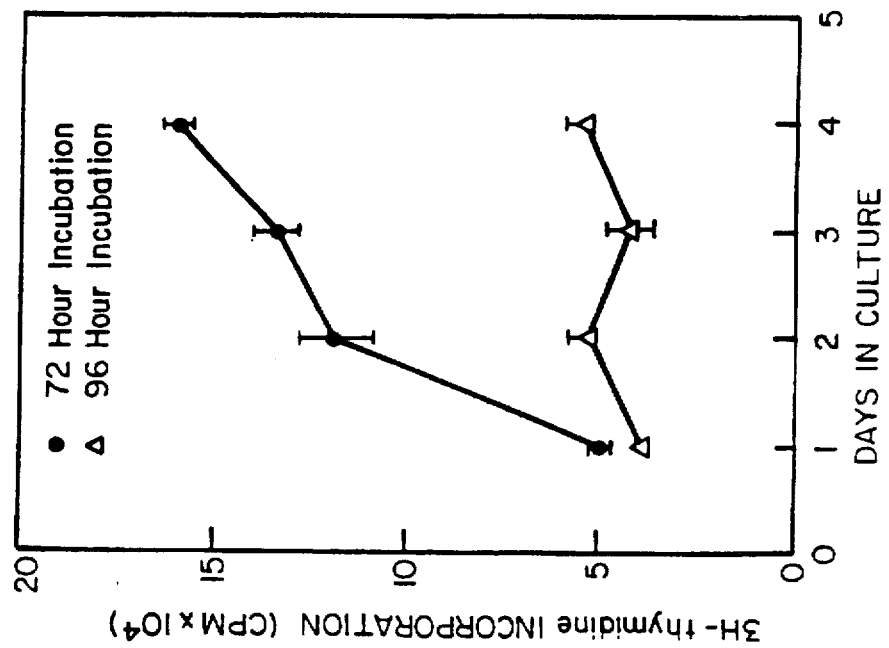
FIG_7A

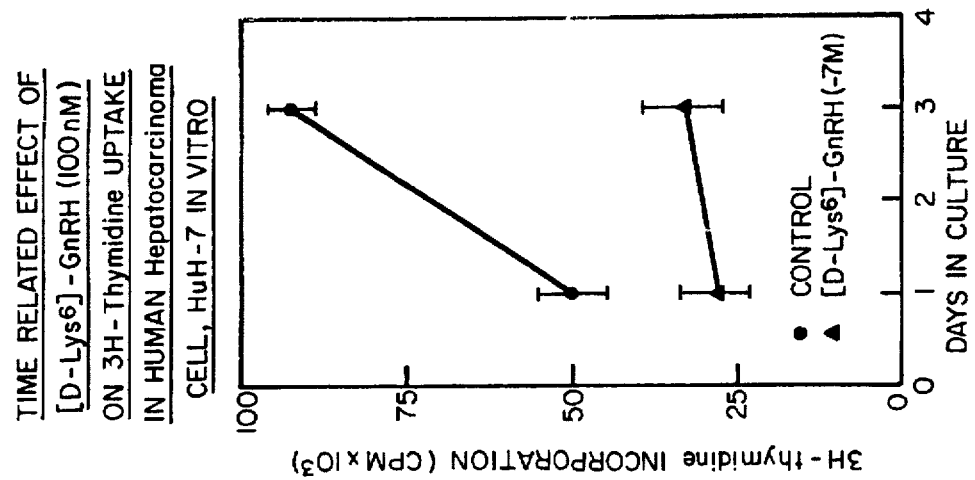
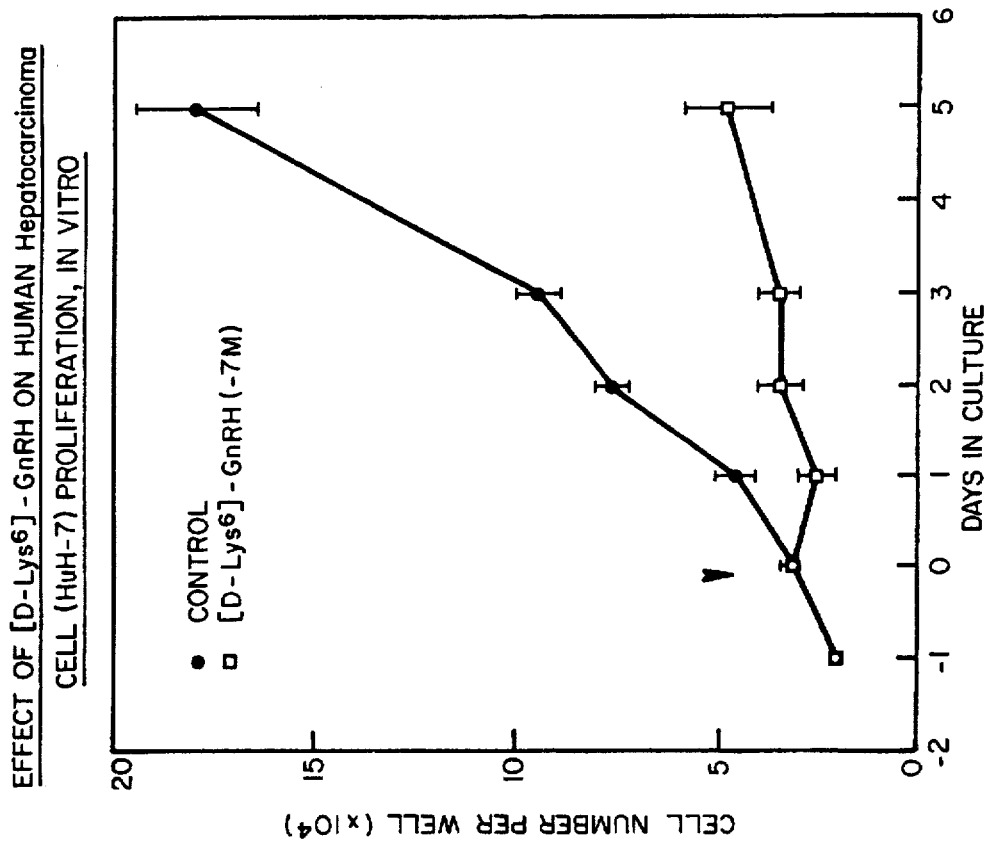

INHIBITION OF LIVER CANCER BY THE USE OF GNRH AND GNRH ANALOGS

FIELD OF THE INVENTIONS

This invention relates to the use of GnRH and GnRH analogs to inhibit liver cancer by the suppression of cell growth.

REFERENCES

The following references are cited in the application as numbers in brackets ([ ]) at the relevant portion of the application.

1. T. Yano, et al., *Breast Cancer Research and Treatment*, 21:35–45 (1992).
2. H. R. Habibi et al., *Fish Physiol. Biochem.*, 11:43 (1993).
3. W. R. Miller,et al., *Nature (London)*, 313:231 (1992).
4. S. R. Milovanovic, et al., *The Prostate*, 20:269–280 (1992).
5. K. A. Eidne et al., *Science*, 229:989 (1985).
6. M. Fekete et al., *Prostate*, 14:191 (1989).
7. T. Segal-Abramson et al., *Mol. Cell. Endocrinol.*, 85:109 (1992).
8. A. V. Schally et al., *J. Steroid Biochem. Mol. Biol.*, 37:1061 (1990).
9. K. J. Walker et al., *J. Endocrinol.*, 111:349 (1986).
10. D. K. Patel et al., *Biochem. Pharmacol.*, 42:337 (1991).
11. R. P. Millar et al., *J. Biol. Chem.*, 264:21007 (1989).
12. D. Pati et al., *Am. J. Physiol.*, 264:R227 (1993).
13. H. R. Habibi et al., *Biol. Reprod.*, 36:844 (1987).
14. A. DeLean et al., *Am. J. Physiol.*, 235:E97 (1978).
15. P. M. Munson et al., *Anal. Biochem.*, 107:220 (198)).
16. J. H. Zar, *Biostatistical Analysis*(Prentice-Hall, Inc., New Jersey, ed. 2), pp. 186–190 (1984).
17. G. A. McPherson, *J. Pharmacol. Methods*, 14:213–228 (1985).
18. H. Nakabayashi et al., "Growth of Human Hepatoma Cell Lines with Differentiated Functions in Chemically Defined Medium", *Cancer Res.* 42:3858–3863 (1982).

The disclosure of the above publications, patents and patent applications are herein incorporated by reference in their entirety to the same extent as if the language of each individual publication, patent and patent application were specifically and individually included herein.

BACKGROUND OF THE INVENTION

There is increasing evidence that GnRH has extrapituitary effects in a number of peripheral tissues, including ovary, testis, brain, placenta, thymus, and adrenal cortex [2]. A number of studies have demonstrated that various tumors of breast, prostate, ovary, pituitary, and pancreatic origin have specific GnRH binding sites and respond to GnRH analogs, in terms of tumor growth suppression in vitro and in vivo [3,5,6,8]. It has been shown in these studies that in vitro suppression of cell growth and/or proliferation is correlated with the in vivo ability of GnRH and GnRH analogs to suppress tumor growth [1,4].

Experimental evidence indicates that the tumor-suppressing effect of GnRH may be through a mechanism independent of its pituitary gonadotropin-release activity, since GnRH analogs influence the proliferation of cultured human mammary tumor cells (MCF-7) [3,8], Mia PaCa-2 pancreatic cancer cells, and PC-3 and LNCaP human prostate cancer cell lines in vitro [8]. Further, a number of cancer cell lines of breast, prostate and pancreatic origin have been shown to contain specific GnRH binding sites [3,5,6,8] which are apparently coupled to effector molecules through a G-protein mediated mechanism [7]. Moreover, GnRH analogs have been used in clinical studies to suppress breast cancer growth in postmenopausal patients with already low levels of plasma estrogen [9].

No prior study has shown any direct effect of GnRH or its analogs on liver cancer cells. There is a need for a treatment for liver cancer. In particular, a treatment without serious side effects would be preferred.

SUMMARY OF THE INVENTION

One aspect of the invention provides a method of suppressing proliferation or inhibiting the growth of liver cancer cells comprising: selecting a liver cancer cell proliferation inhibiting peptide or peptide-containing compound based on a GnRH amino acid sequence; and administering an inhibitory effective amount of said peptide or peptide-containing compound to said cells.

Another aspect of the invention is a pharmaceutical composition useful for the treatment of liver cancer comprising an inhibitory effective amount of at least one liver cancer cell proliferation inhibiting peptide or peptide-containing compound based on a GnRH amino acid sequence; and a pharmaceutically acceptable carrier.

A further aspect of the invention provides a method for diagnosing liver cancer comprising: obtaining a biological sample comprising hepatic cells suspected of being neoplastic; contacting said biological sample with at least one peptide or peptide-containing compound based on a GnRH amino acid sequence under conditions wherein binding to GnRH receptors occurs; and detecting whether or not said peptide or peptide-containing compound binds to said cells with Kd (equilibrium dissociation constant) smaller than 30 nM, wherein said binding to said cells indicates the presence of GnRH receptors on said cells, denoting that said cells are neoplastic.

A still further aspect of the invention provides a method for diagnosing liver cancer comprising: obtaining a biological sample comprising hepatic cells suspected of being neoplastic; contacting said biological sample with at least one antibody to a GnRH receptor sequence under conditions wherein antibody binding to said GnRH receptor sequence occurs; and detecting whether or not said antibody binds to said cells, wherein binding to said cells indicates the presence of GnRH receptors on said cells, denoting that said cells are neoplastic.

BRIEF DESCRIPTION OF THE DRAWINGS

FIGS. 1A, 1B and 1C illustrate the effect of GnRH peptides on HepG2 cell proliferation.

FIGS. 2A, 2B, 2C and 2D illustrate displacement curves for binding of GnRH peptides to HepG2 and non-cancerous human liver cell membrane preparations.

FIG. 3 illustrates that the effect of GnRH peptides on HepG2 cell proliferation was similar regardless of whether a single or multiple administration was used.

FIG. 4 illustrates the dose related effect of GnRH peptides on HepG2 cell proliferation.

FIG. 5 illustrates that the effect of GnRH peptides on HepG2 cell proliferation is relatively long lasting, and continues to suppress proliferation after addition of GnRH antagonist or removal of GnRH agonist following three days of treatment with [D-Lys$^6$]-GnRH.

FIGS. 6A, 6B, 6C and 6D illustrate the binding characteristics of the HepG2 GnRH receptor.

FIGS. 7A and 7B illustrate the effect of [D-Lys$^6$]-GnRH on 3H-thymidine uptake by HepG2 cells.

FIG. 8 illustrates the effect of [D-Lys⁶]-GnRH on HuH-7 cell proliferation.

FIG. 9 illustrates the effect of [D-Lys⁶]-GnRH on 3H-thymidine uptake by HuH-7 cells.

DETAILED DESCRIPTION OF THE INVENTION

The invention described herein relates to the unexpected discovery that GnRH and GnRH analogs inhibit liver cancer, such as hepatoma, by suppressing cell proliferation. It has been found that the human hepatocarcinoma derived cell line HepG2 and the human hepatoma derived cell line HuH-7 contain gonadotropin releasing hormone (GnRH) receptors, and respond to various molecular forms of GnRH in terms of suppressed cell proliferation.

Certain fish GnRH molecules, such as lamprey GnRH which has little gonadotropin (luteinizing hormone) releasing activity in mammals, suppress HepG2 and HuH-7 cell proliferation with similar potency to superactive mammalian GnRH analogs. These forms of GnRH have little effect on human pituitary gonadotropin release, gonadal steroidogenesis, and reproductive functions generally. Thus, the use of such forms of GnRH in the present invention has the added advantage that they will have few side effects.

A. Definitions

As used herein the following terms have the following meanings: "Amino acid" means any one of the molecules that serve as building blocks for making a polypeptide (protein). As used in this application, the term amino acid includes both natural amino acids, i.e., those found in nature, non-natural amino acids, i.e., synthetic amino acids not found in nature, and amino acid derivatives, i.e., chemically modified natural or non-natural amino acids. In the peptides shown herein, each amino acid residue is in the L- form if not otherwise specified, and is given its standard three letter symbol according to the following conventional list:

| Amino Acid Name | 3 Letter Symbol |
| --- | --- |
| Alanine | Ala |
| Asparagine or aspartic acid | Asx |
| Cysteine | Cys |
| Aspartic acid | Asp |
| Glutamic acid | Glu |
| Phenylalanine | Phe |
| Glycine | Gly |
| Histidine | His |
| Isoleucine | Ile |
| Lysine | Lys |
| Leucine | Leu |
| Methionine | Met |
| Asparagine | Asn |
| Proline | Pro |
| Glutamine | Gln |
| Arginine | Arg |
| Serine | Ser |
| Threonine | Thr |
| Valine | Val |
| Tryptophan | Trp |
| Tyrosine | Tyr |
| Glutamine or glutamic acid | Glx |
| pyroGlutamic acid | pGlu |

"Antibody" means a molecule that binds to a known antigen.

"Biological sample" means a sample of mammalian cells. These cells may be part of a tissue or organ sample obtained, for example, by biopsy, or they may be individual cells, for example, blood cells or cells grown in tissue culture.

"Cancerous cell" means a cell in or from a neoplasm.

"Cell proliferation inhibiting peptide compound" means a peptide or peptide-containing compound which inhibits cell proliferation, either in vitro or in vivo.

"GnRH-related peptide", "GnRH peptide", "GnRH analog", "GnRH antagonist", "GnRH agonist", and "GnRH superagonist" mean a peptide or peptide-containing compound based on a GnRH amino acid sequence. It has been found that amino acid positions 1, 2, 3, and 4 of GnRH and related peptides are important for biologic activity in terms of pituitary gonadotropin (LH) release. Thus, GnRH antagonists may have changes in these positions which allow binding to GnRH receptors, blocking native GnRH activity. GnRH agonists may have changes in the 5 position, as it has been found that modification here may be important to desensitization. It has been found that changes at positions 6 and 9 can be used to increase the metabolic stability of GnRH-related peptides. Thus, GnRH agonists and superagonists are often modified at these amino acid residues. The amino acid in position 10 may be removed in some GnRH-related peptides, including superagonists. Removal of the amino acid in position 10 coupled with addition of a protective group to the amino acid in position 9 has been found to increase biologic stability.

"Gonadotropin-Releasing Hormone" or "GnRH", also known as luteinizing hormone-releasing hormone or LH-RH, means a decapeptide found in the hypothalamus which causes the release of various other hormones such as gonadotropin, follicle stimulating hormone, etc. The structure of mammalian, including human, GnRH is: pGlu-His-Trp-Ser-Tyr-Gly-Leu-Arg-Pro-Gly-NH₂ (SEQ ID NO 1).

"Growth" means progression through the cell cycle with the result that two daughter cells are formed from each mother cell.

"Hepatocarcinoma" or "hepatoma" mean liver cancer, i.e., any of various malignant neoplasms of the liver. In particular, they are meant to include hepatocellular or liver cell carcinoma.

"Label" means to incorporate into a compound a substance that is readily detected. Such substances include radioactive substances and fluorescent dyes, for example.

"Neoplastic" means the related to the process resulting in the formation and growth of an abnormal tissue that grows by cellular proliferation more rapidly than normal, and continues to grow after the stimuli that initiated the new growth cease.

"Normal cell" means a non-cancerous cell.

"Proliferation" means growth and reproduction, i.e., division of cells.

B. Synthesis and Methodology

With regard to the preparation of GnRH, GnRH analogs, GnRH antagonists, and GnRH-related peptides which are useful in the present invention, many of these compounds are available from commercial sources such as Sigma and Peninsula Laboratory, Inc. (Belmont, Calif.). Analogs not commercially available as standard products may be synthesized using standard peptide synthesis techniques well known to those in the art. (Such methods may be found, for example, in J. Stewart and J. Young, Solid Phase Peptide Synthesis, 2nd Edition, Pierce Chemical Co., 1984.)

Various GnRHs, may also be purchased, for example, from Peninsula, and radiolabelled with $I^{125}$ label on a particular amino acid. Methods of preparing such compounds are well known in the art [12].

In general, GnRH is a peptide composed of ten amino acids. The structure of mammalian, including human, GnRH is: pGlu-His-Trp-Ser-Tyr-Gly-Leu-Arg-Pro-Gly-NH$_2$ (SEQ ID NO 1). Positions 7 and 8 of GnRH and GnRH-related peptides are important for receptor binding, and this binding domain often indicates species specificity. For example, the structure of lamprey GnRH is: pGlu-His-Tyr-Ser-Leu-Glu-Trp-Lys-Pro-Gly-NH$_2$ (SEQ ID NO 2).

It has unexpectedly been found that human liver cancer cells recognize the GnRH binding domain for GnRH-related peptides. In particular, it has been found that liver cancer cells recognize the binding domain for fish GnRHs, including lamprey GnRH. This binding domain is not recognized to the same extent by human pituitary cells in vitro or in vivo.

GnRH, its analogs and antagonists and related peptides are widely used for gonadotropin hormone therapy and for treatment of hormone related cancers. It has been found that positions 1, 2, 3, and 4 are important for biologic activity in terms of pituitary gonadotropin (LH) release. Thus, GnRH antagonists may have changes in these positions which allow binding to GnRH receptors, blocking native GnRH activity. GnRH agonists may have changes in the 5 position, as it has been found that modification here may be important to desensitization, i.e., may decrease desensitization, leading to decreased hormone levels.

It has been found that changes at positions 6 and 9 can be used to increase the stability of GnRH-related peptides. Thus, GnRH agonists and superagonists are often modified at these amino acid residues. Use of derivatized amino acids or D-amino acids in the 6 position may protect against proteolytic degradation, thus increasing the activity of a GnRH-related peptide. The amino acid in position 10 may be removed in some GnRH-related peptides, including superagonists. Removal of the amino acid in position 10 coupled with addition of n-ethylamide or other protective group to the amino acid in position 9 has been found to increase biologic stability.

It is expected that several GnRH-related peptides will be useful in the present invention. In particular, GnRH, GnRH analogs and GnRH-related peptides which are effective in suppressing the proliferation of liver cancer cells but which do not have hormonal side effects, e.g. those peptides which have no effect on the pituitary, are preferred.

GnRH and GnRH analogs based on the lamprey GnRH amino acid sequence are more preferred due to their lack of pituitary effect and high binding to liver cancer cells. Lamprey GnRH and GnRH analogs with modifications at positions 6 and 9, which modifications do not affect liver cancer cell inhibitory activity but which render the compound more stable metabolically, are especially preferred. Such compounds have the structure: pGlu-His-Tyr-Ser-Leu-Xaa6-Trp-Lys-Xaa9-Gly-NH$_2$ (SEQ ID NO 3) where Xaa6 may be any derivatized amino acid (D- or L-form) or any D-amino acid, and especially D-Lys or D-Leu; and Xaa9 may be Pro, any D-amino acid, any non-natural amino acid (D- or L-form), or any derivatized amino acid (D- or L-form). Also especially preferred are decapeptide compounds of the structure: pGlu-His-Tyr-Ser-Xaa5-Xaa6-Xaa7-Xaa8-Xaa9-Gly-NH$_2$ (SEQ ID NO 11) where Xaa6 and Xaa9 are as in SEQ ID NO 3 and Xaa7 may be any D- or L-natural or non-natural amino acid or derivative, and especially Leu or Trp, Xaa8 may be any D- or L-natural or non-natural amino acid or derivative, and especially Asn, and Xaa5 may be any D- or L-natural or non-natural amino acid or derivative, and especially His.

Especially preferred compounds also include nonapeptide compounds with the structure: pGlu-His-Tyr-Ser-Leu-Xaa6-Trp-Lys-Xaa9-R (SEQ ID NO 4) where Xaa9 may be Pro, any D-amino acid, any non-natural amino acid (D- or L-form), or any derivatized amino acid (D- or L-form) and Xaa6 may be any derivatized amino acid (D- or L-form) or any D- amino acid, and especially D-Lys or D-Leu. In a preferred embodiment, Xaa9 is Pro, and R is selected from the group consisting of —NH$_2$, n-ethylamide, hydrocarbyl amides of from 1 to about 6 carbon atoms, and other pharmaceutically acceptable blocking groups which protect against metabolic degradation. Also especially preferred are nonapeptide compounds of the structure: pGlu-His-Tyr-Ser-Xaa5-Xaa6-Xaa7-Xaa8-Xaa9-R (SEQ ID NO 12) where Xaa9, Xaa6 and R are as in SEQ ID NO 4 and Xaa7 may be any D- or L-natural or non-natural amino acid or derivative, and especially Leu or Trp, Xaa8 may be any D- or L-natural or non-natural amino acid or derivative, and especially Asn, and Xaa5 may be any D- or L-natural or non-natural amino acid or derivative, and especially His.

Synthesis of all the above mentioned GnRHs, GnRH analogs, GnRH agonists, GnRH antagonists, and GnRH-related peptides may be accomplished by routine peptide synthesis and derivatization methods well known to those of skill in the art. (Such methods may be found, for example, in J. Stewart and J. Young, Solid Phase Peptide Synthesis, 2nd Edition, Pierce Chemical Co., 1984.)

C. Pharmaceutical Compositions

The methods of this invention are achieved by using a pharmaceutical composition comprising one or more cell proliferation inhibiting GnRH, GnRH analog, or GnRH-related peptides or peptide-containing compounds.

Parenteral administration is preferred, with subdermal or intramuscular administration most preferred. Intravenous administration or use of implanted milliosmol pumps (available from Alza) may also be used.

When used for parenteral administration, which is preferred, the GnRH-related peptides of the present invention may be formulated in a variety of ways. Aqueous solutions of the peptides of the present invention may be encapsulated in polymeric beads, liposomes, nanoparticles or other injectable depot formulations known to those of skill in the art. (Examples thereof may be found, for example, in Remington's Pharmaceutical Sciences, 18th Edition, 1990.)

Compositions including a liquid pharmaceutically inert carrier such as water may also be considered for both parenteral and oral administration. Other pharmaceutically compatible liquids may also be used. The use of such liquids is well known to those of skill in the art. (Examples thereof may be found, for example, in Remington's Pharmaceutical Sciences, 18th Edition, 1990.)

Doses are selected to provide effective inhibition of liver cancer cell growth and/or proliferation. Useful doses are expected to be from about 0.005 to 0.5 mg/kg/month for depot injections, preferably about 0.05 mg/kg/month. When daily administration is used, useful doses are expected to be from about 0.0002 to 0.02 mg/kg/day, preferably about 0.001 to 0.003 mg/kg/day.

The dose level and schedule of administration may vary depending on the particular GnRH-related compound(s) and/or compositions used, the method of administration, and such factors as the age and condition of the subject.

As discussed previously, parenteral administration is preferred, but formulations may also be considered for other means of administration such as orally, per rectum, and transdermally. The usefulness of these formulations may depend on the particular compound used and the particular subject receiving the GnRH-related compound.

Oral formulations of GnRH-related compounds may optionally and conveniently be used in compositions containing a pharmaceutically inert carrier, including conventional solid carriers, which are conveniently presented in tablet or capsule form. Formulations for rectal or transdermal use may contain a liquid carrier that may be oily, aqueous, emulsified or contain certain solvents suitable to the mode of administration. Suitable formulations are known to those of skill in the art. (Examples thereof may be found, for example, in Remington's Pharmaceutical Sciences, 18th Edition, 1990.)

D. Use of GnRH and GnRH-Related Peptides for Inhibition of Liver Cancer

The present invention is drawn to the unexpected discovery that various GnRH-related peptides have direct action on the proliferation of liver cancer cells. In particular, GnRH-related peptides suppressed proliferation of the human hepatoma derived cell lines HepG2 and HuH-7.

The HepG2 cell line, an immortalized hepatoma cell line of human origin, retains many of the specialized cellular functions lost by primary hepatocytes in culture, such as expression of hepatocyte-specific cell surface receptors, as well as synthesis and secretion of major plasma proteins [10]. HepG2 Cells were grown under standard conditions as described herein. Single administration of [D-Lys$^6$]-GnRH (available from Sigma, catalog number L 5022) at $10^{-7}$M or repeated administration of [D-Lys$^6$]-GnRH at $10^{-7}$M every two days significantly suppressed HepG2 cell growth in a similar fashion over a period of six days in culture. (See FIG. 3.) These results showed that a single treatment of the cells with the peptide was essentially equivalent to administration every two days.

The HuH-7 cell line is an immortalized human hepatoma cell line which has been well characterized [18]. HuH-7 cells were grown under standard conditions as described herein. Single administration of [D-Lys$^6$]-GnRH at $10^{-7}$M significantly suppressed HuH-7 cell growth over a period of six days in culture. (See FIG. 8.)

HepG2 cells showed specificity of GnRH action. This was shown by: 1) the lack of effect of α-melanocyte stimulating hormone (α-MSH), a non-GnRH-related peptide, on HepG2 proliferation (FIG. 1C); and 2) total inhibition of GnRH-mediated effects on HepG2 cell proliferation by various GnRH antagonists (FIG. 1B). The [D-Lys$^6$]-GnRH-mediated suppression of HepG2 cell proliferation was completely inhibited by addition of GnRH antagonists, such as [DpGlu$^1$, DPhe$^2$, DTrp$^{3,6}$]-GnRH (DpGlu-DPhe-DTrp-Ser-Tyr-DTrp-Leu-Arg-Pro-Gly-NH$_2$; SEQ ID NO 5) or Antide (Acetyl-β-[2-Napthyl]-D-Ala-D-p-Chloro-Phe-β-[3-pyridyl]-D-Ala-Ser-NE-[Nicotinoyl]-Lys-NE-[Nicotinoyl]-D-Lys-Leu-NE-[Isopropyl]-Lys-Pro-D-Ala-NH$_2$; SEQ ID NO 6), suggesting the involvement of specific GnRH receptors. The antagonists themselves did not have any effect on HepG2 cell proliferation (FIG. 1B).

The effect of various GnRH peptides on HepG2 cell proliferation can essentially be divided into two phases: 1) growth phase (days 0–4) and 2) static phase (days 4–6). During growth phase, GnRH treatment significantly reduced HepG2 proliferation as evidenced by slower doubling time (control=40.0±2.8 hrs vs. [D-Lys$^6$]-GnRH-treated (1000 nM)=105.0±10.0 hrs). The GnRH-treated cells entered the static phase after 4 days of culture, whereas the control group continued proliferation until they reached confluence after approximately 6 days of culture. The maximum cell proliferation in the GnRH-treated groups was less than 40% of that reached by the control group during the period of 6 days. That is to say, GnRH treatment resulted in greater than 60% inhibition of total cell proliferation. The dose related inhibitory effect of GnRH peptides on HepG2 cell proliferation was clearly seen at the end of the growth phase (days 3 and 4). The ED$_{50}$ values are shown in Table 1. The dose-related effect of GnRH was less apparent after 2 days of additional culture in the static phase.

The dose-related effect of GnRH is also by doubling time, which is slower at higher concentrations of GnRH. Doubling time values for 10, 100 and 1000 nM [D-Lys$^6$]-GnRH were 65 ±4.9 hrs, 77 ±6.7 hrs and 105 ±10.0 hrs, respectively; calculated over 4 days of growth. The doubling time of GnRH-treated cells can not be estimated during the static phase, since proliferation is arrested (i.e., doubling time is infinite), whereas control cells continue to grow until they reach confluence beyond day 6.

The effect of GnRH can not be reversed by removing GnRH from the medium or by adding a GnRH antagonist after three days of treatment with [D-Lys$^6$]-GnRH (FIG. 5). Further, the effect of GnRH was not caused by cytotoxic activity, since cellular viability determined by trypan blue exclusion (>90%) did not change following treatments with various GnRH molecules. It would therefore appear from our results, without being bound to any theory, that GnRH-treated cells undergo a transition into a cytostatic phase which continues without a requirement for the presence of GnRH.

Treatment with a number of GnRH molecular forms, including [D-Lys$^6$]-GnRH (SEQ ID NO 7), mammalian GnRH (GnRH; SEQ ID NO 1), salmon GnRH ([Trp$^7$, Leu$^8$]-GnRH; sGnRH; SEQ ID NO 8) lamprey GnRH ([Tyr$^3$, Leu$^5$, Glu$^6$, Trp7, Lys8]-GnRH; lGnRH; SEQ ID NO 2) and catfish GnRH ([His$^5$,Asn$^8$]-GnRH; cfGnRH; SEQ ID NO 9) at $10^{-7}$M suppressed HepG2 cell proliferation over a 6 day period of experiment (FIG. 1C).

The effect of these GnRH peptides were found to be dose-related over a range of 1–1000 nM. See Table 1 for ED$_{50}$ values.

While after 4 days of treatment the ED$_{50}$value for sGnRH was significantly (P<0.05) higher than lGnRH, after 6 days of culture with $10^{-7}$M all GnRH molecular forms inhibited HepG2 cell proliferation to the same extent. However, the same GnRH peptides have significantly different potency in terms of gonadotropin (luteinizing hormone) release in the pituitary of mammals. In particular, lGnRH, exerts little gonadotropin release activity in rat and sheep pituitary [11]. Thus, this GnRH peptide has minimal effect on pituitary hormone production. Binding affinity for these peptides is different in normal pituitary cells as compared to normal liver cells. (See Table 1.) The data in Table 1 show a large difference between normal pituitary cell GnRH receptors and GnRH receptors in HepG2 cells. This difference may be important in the mechanism of GnRH-induced suppression of hepatocarcinoma cell proliferation.

Specific GnRH binding was observed in the membrane fraction prepared from HepG2 cells using radioiodinated mammalian ($^{125}$I-[D-Lys$^6$]-GnRH; SEQ ID NO 7) and salmon ($^{125}$I-[D-Arg$^6$, Trp$^7$, Leu$^8$, Pro$^9$-NEt]-GnRH; sGnRH-A; SEQ ID NO 10) GnRH analogs using methods described herein. The binding of both GnRH ligands to HepG2 membrane preparation was found to be displaceable (FIGS. 2A and 2B), saturable, reversible and dependent on time, temperature and tissue concentration (FIGS. 6A to 6D).

Hill plot as well as Scatchard analysis of the saturation and homologous displacement curves, using either $^{125}$I-[D-Lys$^6$]-GnRH or $^{125}$I-sGnRH-A as labeled ligand, indicated the presence of one class of high affinity GnRH binding sites in the HepG2 cells. Five of seven competition curves could satisfactorily be fitted using a single site model (FIG. 2A). However, four out of seven curves could also be fitted to a two site model, consisting of two classes of binding sites, a high affinity/low capacity (equilibrium dissociation constant; $K_d$=0.08±0.78 nM) and low affinity/high capacity ($K_d$=0.50±4.17 nM) sites.

Although statistical analysis did not indicate a significant difference between one site and two site fit, we were unable to fit a two site model to a number of other GnRH peptides used in the competition studies. The ED$_{50}$ value obtained from the dose response curve for [D-Lys$^6$]-GnRH on HepG2 cell proliferation over a period of 4 days was consistent with the observed $k_d$ values obtained from the one site fit model. See Table 1. While all these factors favor the presence of a single class of high affinity GnRH binding sites in the HepG2 cells, we can not totally rule out the presence of two classes of GnRH binding sites.

Non-cancerous human cells (FIGS. 2C and 2D) and normal rat liver cells (Table 1) had only a single class of binding sites. The affinity of this class of binding sites was three and two orders of magnitude lower, respectively, than the affinity of binding sites of HepG2 cells. These data indicate that high affinity hepatic GnRH binding sites may only be expressed in cancerous cells. The $k_d$ values for normal human and rat liver and normal pituitary for various GnRH-related peptides were found to be different from those observed in HepG2 cells, as summarized in Table 1.

The binding of GnRH to HepG2 cells and non-cancerous human, and rat liver was specific. Various unrelated neuropeptides such as α-MSH, Thyrotropin releasing hormone (TRH) and Met Enkephalin did not displace labeled [D-Lys$^6$]-GnRH (FIGS. 2B and 2D). The affinity of GnRH binding to HepG2 membrane preparation ($k_d$=9.17 nM) is close to that reported for human ductal breast tumor membrane ($k_d$=20 nM) [5] and pituitary GnRH receptors ($k_d$=4.76 nM) [5], as well as high affinity binding sites in a human mammary cancer cell (MCF-7; $k_d$=1.4 nM), and rat mammary tumor membranes ($k_d$=2.5 nM) [7]. A number of fish GnRH peptides bound to HepG2 cells with greater affinity than to normal rat liver and pituitary cells (Table 1). This indicates a difference in GnRH receptor molecules in liver cancer cells, compared to normal pituitary and liver cells. The observed high affinity for fish GnRH peptides in HepG2 cells was consistent with their action in suppressing the growth of the same cells in vitro. Both sGnRH and lGnRH have significantly lower potency in releasing gonadotropin from mammalian pituitary compared to mammalian based GnRH analogs [11]. Therefore, GnRH-related peptides based on certain fish GnRH molecules may be especially useful as tumor suppressor agents with minimal effect on pituitary gonadotropin release. Use of "pituitary-inert" GnRH analogs will reduce the side effects that may arise from treatment with high doses of GnRH analogs in human.

GnRH agonists, including a number of fish GnRH-related peptides, clearly suppress the proliferation of HepG2 cells, and will be useful to provide an effective chemotherapy for treatment of human liver cancer.

The present invention also has diagnostic use, since we have found that liver cancer cells have receptors which have high binding affinity for GnRH, in that they bind GnRH and its analogs with equilibrium dissociation constant (kd) lower than 30 nM, as determined in a homologous displacement assay using $^{125}$I-[D-Lys$^6$]-GnRH as labeled and [D-Lys$^6$]-GnRH as unlabeled ligand.

Non-cancerous human liver cells contain low affinity GnRH binding sites (kd greater than 3000 nM) and normal rat liver cells contain GnRH binding sites with kd greater than 700 nM. Among tissues of liver origin, only cancerous cells, e.g., hepatocarcinoma or hepatoma cells, had GnRH binding sites with kd less than 30 nM. Thus, there is a strong correlation between the levels of high affinity GnRH binding sites and the neoplasticity of liver cells.

Thus, simple immunochemical staining of cells or sections of cells should give an accurate estimate of the portion of cells with such GnRH receptor/binding sites, and, therefore, the prevalence of neoplastic liver cells. Such tests, based on the production and use of anti-GnRH antibodies and standard secondary techniques of visualization will be useful in liver cancer diagnosis and might also be useful to the scientific research community.

A further immunohistochemical test that may be used for liver cancer diagnosis involves assay of biopsy material. These tests would use antibodies against human liver cancer high affinity GnRH receptors. Such a test might also be useful to the scientific research community.

In a diagnostic method of the present invention, a biological sample comprising liver cells or liver cell membrane receptors obtained from an individual or a culture are processed in order to determine the extent to which they show high binding affinity for GnRH. This can be determined using known techniques and an antibody specific for GnRH. Comparison of results obtained from cells or receptor preparations being analyzed with results obtained from an appropriate control (e.g., normal cells or membrane preparations of the same type) is carried out. High affinity GnRH binding is indicative of an increased probability of abnormal cell proliferation or oncogenesis or of the actual occurrence of abnormal proliferation or oncogenesis. Such antibodies to GnRH will generally be detectably labelled (e.g., with a radioactive label, a fluorescent material, biotin or another member of a binding pair or an enzyme).

In a further diagnostic method of the present invention, a biological sample comprising liver cells or liver cell membrane receptors obtained from an individual or a culture are processed in order to determine the presence of high affinity GnRH binding sites. This can be determined using known techniques. Comparison of results obtained from cells or receptor preparations being analyzed with results obtained from an appropriate control (e.g., normal cells or membrane preparations of the same type) is carried out. Increased GnRH binding affinity (1/kd) is indicative of an increased probability of abnormal cell proliferation or oncogenesis or of the actual occurrence of abnormal proliferation or oncogenesis. Ligands for such GnRH receptor assays may be produced as described [12]. Such GnRH analogs will generally be detectably labelled (e.g., with a radioactive label, a fluorescent material, biotin or another member of a binding pair or an enzyme).

Antibodies specifically reactive with GnRH or liver cancer GnRH receptors can be produced, using known methods. For example, anti-GnRH or anti-GnRH receptor antisera can be produced by injecting an appropriate host (e.g., rabbits, mice, rats, pigs) with either GnRH or GnRH receptor protein, possibly coupled to bovine serum albumin (BSA) or another immunogenic protein, and withdrawing blood from the host animal after sufficient time for antibodies to have been formed. Monoclonal antibodies can also be produced using known techniques.

The following examples are offered to illustrate this invention and are not meant to be construed in any way as limiting the scope of this invention.

E. Examples

The following methods were used to perform the studies described herein.

1. Culture of HepG2 and HuH-7 Cells

HepG2 or HuH-7 cells were maintained in 75-cm$^2$ flasks at 37° C. under a humidified atmosphere of 5% $CO_2$ in modified Minimum Essential Medium (Gibco-BRL) supplemented with 10% fetal bovine serum, 200mM 1-Glutamine (1%), Penicillin (1000 IU/ml), streptomycin (100 μg/ml) and sodium bicarbonate (0.15%). Cells grown to confluence were harvested following mild trypsinization and wash (twice by slow centrifugation; 400 g for 10 minutes) in normal culture medium.

Approximately 50,000 cells in 1.0 ml culture media were plated in 24 deep well plates (Flacon). This time was considered day −1. Cells were allowed to grow for one day. The growing cells were then treated with various hormones (at day 0) prepared aseptically in culture media immediately prior to addition. The final volume was maintained at 1 ml. The plates were then incubated at 37° C. for a period of 4 to 6 days, as described above.

Cells in each well were harvested by removal of culture media and incubation with 0.5 ml 0.25% trypsin and 1.75 mM EDTA for 30 minutes at 37° C. Cells were then transferred into 1.5 ml microfuge tubes and centrifuged at 100g for 10 minutes. The supernatant was removed and the pellet was resuspended in a final volume of 200 μl of culture media containing 10% trypan blue.

Cells were then counted using a hemocytometer. The average cell mortality was less than 5.0% and was not different among different treatment groups. Each value represents the mean and standard error of several experiments (n>3), each carried out in quadruplicate incubations at each time point and hormone concentration.

2. GnRH In Vitro Binding

Cells were grown to confluence as previously described and harvested from the flasks by using a rubber policeman. The cells were washed in normal assay buffer ((10 nM Tris[hydroxymethyl] aminomethane[Tris]-HCl), containing 1 mM dithiothreitol and 0.5% BSA [fraction-V] (pH 7.6)) and precipitated by centrifugation at 500g for 5 minutes at 4° C.

The cleaned cells were homogenized in 50 ml of freshly prepared ice cold 25 mM sucrose in assay buffer containing 1 mM Phenylmethanesulphonyl fluoride and 5 mM Ethylenediaminetetraacetic acid, using a glass TEFLON (polytetra-fluoroethylene) homogenizer, followed by centrifugation at 100 ×g for 5 minutes (4° C.). The supernatant was further centrifuged at 17,000×g for 30 minutes at 4° C., and the pellet (crude membrane preparation) washed briefly and resuspended in the assay buffer (approximately 40–50 μg membrane protein or approximately 1 x 106 cell equivalent per 100 μl).

A similar protocol was used to prepare the membrane from fresh rat and frozen human postmortem liver. In all experiments the final membrane preparation was used in the radioreceptor assay within 45 minutes.

For protein determination, aliquots of crude membrane preparations were washed twice with double distilled water by centrifugation (25,000 ×g) and assayed for protein content, using BSA as the standard. The binding assay was carried out at 4° C.

GnRH binding parameters, including equilibrium dissociation constant ($k_d$; reciprocal receptor affinity) and binding capacity (R) were estimated from a Scatchard plot of competition curves using a computerized non-linear least squares curve-fitting program (LIGAND), as described [15]. The displacement curves were fitted for both single and two classes of binding sites by computer calculated lines, as described [13].

3. 3H-Thymidine Uptake

The cells, treated with or without various doses of [D-Lys$^6$]-GnRH in the media, were incubated at 37°0 C. for a period of 3 to 4 days in 24 well plates. 3H-Thymidine incorporation was measured at various time intervals following treatment with [D-Lys$^6$]-GnRH. One mCi 3H-thymidine (Amersham TRK.120, 102 mCi/mg) was added to each well and was incubated at 37° C. for 4 hours. The media containing unabsorbed 3H-thymidine was aspired off and the cells were washed twice with ice cold phosphate buffered saline (PBS). The cells were then fixed with 5% trichloro acetic acid (TCA) for 20 minutes and washed twice with double distilled water. The fixed cells were solubilized with 0.2 ml NCS tissue solubilizer (Amersham) and counted for radioactivity using a liquid scintillation counter (50% efficiency).

EXAMPLE 1

GnRH Receptor Binding in Normal and Cancerous Cells.

The potency of various GnRH-related peptides in terms of binding (equilibrium dissociation constant; kd) and growth suppression activity in the human hepatocarcinoma derived cell line HepG2 was studied. The effective dose giving 50% maximal response ($ED_{50}$) was calculated at day 4 of growth. GnRH binding studies were performed using the method previously described. Data analysis was performed as described [14,16,17].

The amino acid sequence of the GnRH-related peptides used were as follows: [D-Lys$^6$]-GnRH (pGlu-His-Trp-Ser-Tyr-DLys-Leu-Arg-Pro-Gly-NH$_2$ (SEQ ID NO 7)); GnRH (pGlu-His-Trp-Ser-Tyr-Gly-Leu-Arg-Pro-Gly-NH$_2$ (SEQ ID NO 1)); sGnRH (salmon) (pGlu-His-Trp-Ser-Tyr-Gly-Trp-Leu-Pro-Gly-NH$_2$ (SEQ ID NO 8)); lGnRH (Lamprey) (pGlu-His-Try-Ser-Leu-Glu-Trp-Lys-Pro-Gly-NH$_2$ (SEQ ID NO 2)); cfGnRH (catfish) (pGlu-His-Trp-Ser-His-Gly-Leu-Asn-Pro-Gly-NH$_2$ (SEQ ID NO 9)); and [D-Arg$^6$]-sGnRH-A (pGlu-His-Trp-Ser-Tyr-DArg-Trp-Leu-Pro-N-ethylamide (SEQ ID NO 10)).

TABLE 1

Binding of GnRH-Related Peptides

| | Receptor Binding Activity (Kd, nM) | | | | Suppression of HepG2 growth ED$_{50}$(nM)* |
|---|---|---|---|---|---|
| | HepG2 | Normal Human Liver | Normal Rat Liver | Normal Rat Pituitary | |
| Labeled Ligand: $^{125}$I-[D-Lys$^6$]-GnRH | | | | | |
| [D-Lys$^6$]-GnRH | 9.17 (2.8–30.5) | 3300 (1963–5545) | 769 (300–1966) | 0.097 (0.03–0.34) | 2.00 ± 0.93$^{ab}$ |
| GnRH | 13.16 (3.4–50.5) | 5260 (2133–12970) | 384 (301–489) | 3.02 (2.61–3.49) | 4.56 ± 0.97$^{ab}$ |
| sGnRH | 58.80 (18.6–185.4) | 7140 (2974–17139) | 1560 (248–9776) | 179 (108.7–294.8) | 7.55 ± 4.50$^b$ |
| lGnRH | 66.60 (18.01–245.4) | 6660 (1322–33540) | 8330 (5540–12523) | 2.00 (1.66–2.40) | 1.5 ± 0.80$^a$ |
| cfGnRH | 17.85 (8.2–38.4) | N/A | 8330 (6793–10213) | 140 (32.8–597.3) | 2.29 ± 1.41$^{ab}$ |
| Labeled Ligand: $^{125}$I-[D-Arg$^6$]-sGnRH-A | | | | | |
| [D-Arg$^6$]-sGnRH-A | 7.09 (1.2–40.1) | 3846 (1649–8969) | 833 (300–2308) | 0.334 (0.07–1.67) | N/A |

*The ED$_{50}$ Values at days 3 and 4 of growth are not significantly different. The ED$_{50}$ values were analyzed using a one-way analysis of variance with multiple comparison of means (Tukey's) as described [16, 17]. Values with dissimilar superscripts are significantly different (p < 0.05) and Kd values in parentheses are 95% confidence intervals, determined as described [16, 17].

EXAMPLE 2
Effect of GnRH-Related Peptides on HepG2 Proliferation

The effect of GnRH-related peptides on the proliferation of the human hepatoma derived cell line HepG2 was studied. Results are shown in FIGS. 1A to 1C. Values (mean ± SEM) represent the percent change with respect to initial cell number at day 0 over a period of six days in culture.

FIG. 1A shows a dose-dependent effect of the GnRH against [D-Lys$^6$]-GnRH on HepG2 cell growth. The effective dose giving 50% inhibition (ED50) was estimated to be 2.00 ±0.9 nM. This high potency indicates that GnRH agonists can be administered at sufficiently high concentration in vivo to prevent cancer growth.

FIG. 1B shows the effects of GnRH antagonists [D-pGlu$^1$, D-Phe$^2$, D-Trp$^{3,6}$]-GnRH (SEQ ID NO 5) and Antide (Acetyl-β-[2-Napthyl]-D-Ala-D-p-Chloro-Phe-β-[3-pyridyl]-D-Ala-Ser-Ne-[Nicotinoyl]-Lys-NE-[Nicotinoyl]-D-Lys-Leu-NE-[Isopropyl]-Lys-Pro-D-Ala-NH$_2$)(SEQ ID NO 6; available from Sigma) on HepG2 cell proliferation. Administration of these antagonists alone had no effect on HepG2 cell proliferation. The findings indicate that the effect of GnRH-related peptides on HepG2 growth suppression is specific and requires activation of post-receptor mechanisms.

FIG. 1C shows the relative effects of various GnRH-related peptides administered at 10$^{-7}$M as well as a non-GnRH neuropeptide α-MSH (Sigma) on HepG2 cell proliferation. The dose response curves were analyzed by a computerized, four parameter curve fitting program (ALLFIT) as described [14]. The result of time-related response on cell proliferation was analyzed using a two-way ANOVA with multiple comparison means of using computerized statistical package (SYSTAT). Values with dissimilar symbols ($^{a,b,c,d,f,g,h}$) are significantly different (P<0.05) from one another. All GnRH-related peptides inhibited HepG2 cell proliferation, while α-MSH did not. These findings further support specificity of GnRH-related peptide action and demonstrate that GnRH peptides with little potency at the pituitary level can be used to block hepatocarcinoma growth.

EXAMPLE 3
Binding of GnRH-Related Peptides to HepG2 Cells

Homologous displacement of GnRH-related peptides in membrane homogenates prepared from HepG2 cells and non-cancerous postmortem human liver tissue was studied. Values (mean ± SEM) represent specific binding [B/T, bound over total, in %] determined by subtraction of non-saturable binding in the presence of excess peptides (10$^-$sM). Results were obtained from 5 to 7 separated experiments, each carried out in triplicate. The binding data were analyzed by computerized Scatchard analysis (LIGAND) according to Munson and Rodbard [15]. Results are shown in FIGS. 2A to 2D.

FIG. 2A shows the homologous displacement of $^{125}$I-[D-Lys$^6$]-GnRH (SEQ ID NO 7) and $^{125}$I-[D-Arg$^6$, Trp$^7$, Leu$^8$, Pro$^9$-NEt]-GnRH (sGnRH-A; SEQ ID NO 10) bound to HepG2 membrane preparations by unlabeled [D-Lys$^6$]-GnRH and sGnRH-A (Available from Peninsula, Belmont, California, USA). Each of these GnRH-related peptide showed similar displacement. The finding demonstrates potential for the use of non-mammalian GnRH peptides for diagnostic and therapeutic purposes.

FIG. 2B shows the competitive inhibition of $^{125}$I-[D-Lys$^6$]-GnRH (SEQ ID NO 7) binding to HepG2 membrane preparation by unlabeled GnRH (SEQ ID NO 1), sGnRH (SEQ ID NO 8), lGnRH (SEQ ID No 2) (all from Peninsula) and cfGnRH (SEQ ID NO 9). Non-GnRH-related peptides (α-MSH, TRH and Met-Enkephalin) did not show competitive inhibition. These findings demonstrates specificity of GnRH binding to hepatocarcinoma cells.

FIG. 2C shows the homologous displacement of $^{125}$I-[D-Lys$^6$]-GnRH (SEQ ID NO 7) and $^{125}$I-sGnRH-A (SEQ ID NO 10) bound to human liver membrane preparations by unlabeled [D-Lys$^6$]-GnRH and sGnRH-A. Similar displacement of each was shown. These findings demonstrate that the same GnRH-related peptide binds with two orders of magnitude less affinity to non-cancerous human liver cells than to hepatocarcinoma cells. The results indicate that GnRH receptors in human liver cancer cells have different characteristics compared to GnRH binding sites in non-cancerous human liver.

FIG. 2D shows the competitive inhibition of 125I-[D-Lys$^6$]-GnRH (SEQ ID NO 7), sGnRH (SEQ ID NO 8), lGnRH (SEQ ID NO 2) and cfGnRH (SEQ ID NO 9). Again, non-GnRH-related peptides showed no competitive inhibition. These findings further support specificity of GnRH binding.

EXAMPLE 4
Effect of Single and Multiple Administration of GnRH-Related Peptides HepG2 cells were grown under standard conditions as described above. Single administration of [D-Lys$^6$]-GnRH (10⁻⁷M) or repeated administration of the same peptide at 10⁻⁷M every two days (n=8) significantly suppressed HepG2 cell grown in a similar fashion over a period of six days in culture (FIG. 3).

EXAMPLE 5
Dose-Related Effect of GnRH-Related Peptides

FIG. 4 demonstrates HepG2 cell growth suppression in terms of cell number per well at the end of the initial growth phase. The conditions of cell growth and experiments are as described above.

EXAMPLE 6
Effect of Removal and Addition of GnRH Antagonist

Results in FIG. 5 demonstrate that the effect of GnRH cannot be reversed by removing the peptide from the medium or by adding GnRH antagonist after three days of treatment with [D-Lys$^6$]-GnRH. Further, the effect of GnRH was not caused by cytotoxic activity, since cellular viability determined by trypan blue exclusion (>90%) did not change after treatment with various GnRH peptides.

EXAMPLE 7
GnRH Receptor Binding Characteristics

Specific GnRH binding was observed in the membrane fraction prepared from HepG2 cells using $^{125}$I-[D-Lsy$^6$]-GnRH and $^{125}$I-[D-Arg$^6$, Trp$^7$, Leu$^8$, Pro$^9$-NEt]-GnRH; sGnRH-A. The binding of both GnRH ligands to HepG2 membrane preparations were found to be displaceable (FIGS. 2A to 2D), saturable, reversible and dependent on time, temperature and tissue concentration (FIGS. 6A to 6D). GnRH binding parameters, including equilibrium disassociation constant (kd; reciprocal receptor affinity), were estimated from a Scatchard plot of competition curves using a computerized nonlinear least square curve-fitting program (LIGAND) as described [15]. The displacement curves were fitted for both single and two classes of binding sites by computer calculated lines as indicated previously [13]. Five of seven competition curves could satisfactorily be fitted using a single site model. The ED50 value obtained from the dose response curve for [D-Lys$^6$]-GnRH on HepG2 cell proliferation over a period of 4 days is very consistent with the observed $k_d$ values obtained from the Scatchard analysis (see Table 1).

EXAMPLE 8
Effect of GnRH-Related Peptides on 3H-Thymidine Uptake in HepG2 Cells The effect of GnRH-related peptides on $^3$H-thymidine incorporation was tested to assess changes in DNA synthesis of HepG2 cells (FIGS. 7A and 7B). Methods used were as previous described. In the control HepG2 group there was a 250% increase in incorporation of 3 H-thymidine over 4 days of incubation. Treatment with [D-Lys$^6$]-GnRH (10⁻⁷M) blocked further $^3$H-thymidine incorporation above the day 1 level. The [D-Lys$^6$]-GnRH-induced inhibition of DNA synthesis in HepG2 cells was found to be dose-related over the concentration range of 0.1 to 1000 nM (ED50 of 0.18 ±0.03 nM and 0.14 ±0.02 nM after 72 and 96 hours in culture, respectively) (FIGS. 7A and 7B).

EXAMPLE 9
Effect of GnRH-Related Peptides on Proliferation in HuH-7 Cells

HuH-7 cells were grown using the methods previously described. They were treated with [D-Lys$^6$]-GnRH (10⁻⁷M) in the media. The results demonstrate that administration of [D-Lys$^6$]-GnRH totally inhibited HuH-7 proliferation in vitro (FIG. 8).

EXAMPLE 10 Effect of GnRH-Related Peptides on 3H-Thymidine Uptake in HuH-7 Cells The time-related, direct effect of [D-Lys$^6$]-GnRH (10⁻7M) on $^3$H- thymidine incorporation was tested in HuH-7 cells to assess the changes in DNA synthesis of HuH-7 cells (FIG. 9). Treatment with [D-Lys$^6$]-GnRH (10⁻⁷M) blocked further $^3$H-thymidine incorporation above day 1 level.

EXAMPLE 11
Effect of GnRH-Related Peptides on Liver Cancer In Vivo

An in vivo model commonly used as a predictor for anticancer activity in all mammals, such as the athymic nude mouse, will be used. Nude mice will be implanted, e.g. subcutaneously, with an injection of liver cancer cells (e.g., 5M HuH-7 cells) or with a solid xenograft of liver cancer cells.

Mice will receive a GnRH-related peptide, preferably in a depot form. Control mice will not receive a GnRH-related peptide. Treatment with a GnRH-related peptide should inhibit and/or prevent the growth and/or proliferation of liver cancer cells, indicating efficacy or GnRH-related peptides to inhibit liver cancer in mammals.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

---

What is claimed is:

1. A method for suppressing proliferation or inhibiting the growth of liver cancer cells comprising:
    a) selecting a liver cancer cell proliferation inhibiting peptide or peptide-containing compound which has minimal effect on pituitary luteinizing hormone production, wherein said peptide is selected from the group consisting of SEQ ID NOs 3, 4, 11, and 12; and
    b) administering an effective amount of said peptide or peptide-containing compound to said cells, wherein said amount is effective to suppress proliferation or inhibit growth of liver cancer cells.

2. The method of claim 1 wherein said peptide is selected from the group consisting of SEQ ID NOs 3, 4, 11 and 12; and Xaa6 is selected from the group consisting of D-Lys and D-Leu.

3. The method of claim 1 wherein said peptide is selected from the group consisting of SEQ ID NOs 3, 4, 11 and 12; and Xaa9 is Pro.

4. The method of claim 1 wherein said peptide is selected from the group consisting of SEQ ID NOs 4 and 12; and Xaa9 is Pro.

5. The method of claim 1 wherein said peptide is selected from the group consisting of SEQ ID NOs 11 and 12; and Xaa7 is selected from the group consisting of Leu and Trp.

6. The method of claim 1 wherein said peptide is selected from the group consisting of SEQ ID NOs 11 and 12; and Xaa8 is Asn.

7. The method of claim 1 wherein said peptide is selected from the group consisting of SEQ ID NOs 11 and 12; and Xaa5 is His.

8. The method of claim 1 wherein said administration is to a mammal.

9. The method of claim 1 wherein said administration is parenteral.

10. The method of claim 1 wherein said administration is by milliosmol pump.

11. A pharmaceutical composition useful for the treatment of liver cancer comprising:
    a) an effective amount of at least one liver cancer cell proliferation inhibiting peptide or peptide-containing compound which has minimal effect on pituitary luteinizing hormone production, wherein said amount is effective to suppress proliferation or inhibit growth of liver cancer cells and said peptide is selected from the group consisting of SEQ ID NOs 3, 4, 11, and 12; and
    b) a pharmaceutically acceptable carrier.

12. The composition of claim 11 wherein said peptide is selected from the group consisting of SEQ ID NOs 3, 4, 11 and 12; and Xaa6 is selected from the group consisting of D-Lys and D-Leu.

13. The composition of claim 11 wherein said peptide is selected from the group consisting of SEQ ID NOs 3, 4, 11 and 12; and Xaa9 is Pro.

14. The composition of claim 11 wherein said peptide is selected from the group consisting of SEQ ID NOs 4, and 12; and Xaa9 is Pro.

15. The composition of claim 11 wherein said peptide is selected from the group consisting of SEQ ID NOs 11 and 12; and Xaa7 is selected from the group consisting of Leu and Trp.

16. The composition of claim 11 wherein said peptide is selected from the group consisting of SEQ ID NOs 11 and 12; and Xaa8 is Asn.

17. The composition of claim 11 wherein said peptide is selected from the group consisting of SEQ ID NOs 11 and 12; and Xaa5 is His.

18. The composition of claim 11 wherein said composition is suitable for parenteral administration.

19. The composition of claim 11 wherein said pharmaceutically acceptable carrier renders said composition suitable for depot injection.

20. A method for diagnosing liver cancer comprising:

a) obtaining a biological sample comprising hepatic cells suspected of being neoplastic;

b) contacting said biological sample with at least one peptide or peptide-containing compound under conditions wherein binding to GnRH receptors occurs, wherein said peptide is selected from the group consisting of mammalian GnRH; fish GnRHs; lamprey GnRH; and SEQ ID NOs 3, 4, 7, 8, 9, 10, 11, and 12; and c) detecting whether or not said peptide or peptide-containing compound binds to said cells with kd (equilibrium dissociation constant) smaller than 30 nM, wherein said binding to said cells indicates the presence of GnRH receptors on said cells, denoting that said cells are neoplastic.

21. The method of claim 20 wherein said detecting is accomplished using labelled peptide.

22. The method of claim 20, wherein said peptide is selected from the group consisting of mammalian GnRH; fish GnRHs; lamprey GnRH and SEQ ID NOs 7, 8, 9 and 10.

23. The method of claim 20, wherein said peptide is selected from the group consisting of SEQ ID NOs 3 and 4.

24. A method for diagnosing liver cancer comprising:

a) obtaining a biological sample comprising hepatic cells suspected of being neoplastic;

b) contacting said biological sample with at least one antibody to a high affinity GnRH receptor sequence under conditions wherein binding of said antibody to said GnRH receptor sequence occurs; and c) detecting whether or not said antibody binds to said cells wherein said binding to said cells indicates the presence of GnRH receptors on said cells, denoting that said cells are neoplastic.

25. A method for diagnosing liver cancer comprising:

a) obtaining a biological sample comprising hepatic cells suspected of being neoplastic;

b) contacting said biological sample with at least one peptide or peptide-containing compound under conditions wherein binding to high affinity GnRH receptors occurs, wherein said peptide is selected from the group consisting of mammalian GnRH; fish GnRHs; lamprey GnRH; and SEQ ID NOs 3, 4, 7, 8, 9, 10, 11, and 12; and c) detecting whether or not said peptide or peptide-containing compound binds to said cells wherein said binding to said cells indicates the presence of high affinity GnRH receptors on said cells, denoting that said cells are neoplastic.

26. The method of claim 25 wherein said detection is accomplished using antibodies to said peptide or peptide-related compound.

27. The method of claim 26 wherein said antibody is labeled.

28. The method of claim 25, wherein said peptide is selected from the group consisting of mammalian GnRH; fish GnRHs; lamprey GnRH and SEQ ID NOs 7, 8, 9 and 10.

29. The method of claim 25, wherein said peptide is selected from the group consisting of SEQ ID NOs 3 and 4.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Modified-site
    ( B ) LOCATION: 1
    ( D ) OTHER INFORMATION: /label=AA1
        / note= "AA1 is PYROGLUTAMIC ACID"

( x i ) SEQUENCE DESCRIPTION: SEQ ID NO:1:

```
Xaa His Trp Ser Tyr Gly Leu Arg Pro Gly
1             5                   10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /label=AA1
            / note= "AA1 is PYROGLUTAMIC ACID"

( x i ) SEQUENCE DESCRIPTION: SEQ ID NO:2:

```
Xaa His Tyr Ser Leu Glu Trp Lys Pro Gly
1             5                   10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /label=AA1
            / note= "AA1 is PYROGLUTAMIC ACID"

( i x ) FEATURE:
        ( A ) NAME/KEY: Modified-site
        ( B ) LOCATION: 6
        ( D ) OTHER INFORMATION: /label=AA6
            / note= "AA6 may be any D-AA, any AA derivative, and especially D- LYS or D-LEU"

( i x ) FEATURE:
        ( A ) NAME/KEY: Modified-site
        ( B ) LOCATION: 9
        ( D ) OTHER INFORMATION: /label=AA9
            / note= "AA9 may be PRO, any D-AA, any D- or L- non-natural AA or an AA derivative"

( x i ) SEQUENCE DESCRIPTION: SEQ ID NO:3:

```
Xaa His Tyr Ser Leu Xaa Trp Lys Xaa Gly
1             5                   10
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Modified-site
    ( B ) LOCATION: 1
    ( D ) OTHER INFORMATION: /label=AA1
        / note= "AA1 is PYROGLUTAMIC ACID"

( i x ) FEATURE:
    ( A ) NAME/KEY: Modified-site
    ( B ) LOCATION: 6
    ( D ) OTHER INFORMATION: /label=AA6
        / note= "AA6 is any D-AA or any AA derivative, and especially D- LYS or D-LEU"

( i x ) FEATURE:
    ( A ) NAME/KEY: Modified-site
    ( B ) LOCATION: 9
    ( D ) OTHER INFORMATION: /label=AA9
        / note= "AA9 is PRO, any D-AA, any D- or L- non-natural AA or any derivative AA, with or without a hydrocarbyl amide (C1- C6) or other blocking group"

( x i ) SEQUENCE DESCRIPTION: SEQ ID NO:4:

Xaa His Tyr Ser Leu Xaa Trp Lys Xaa
1               5

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /label=AA1
            / note= "AA1 is D-AA, and is PYROGLUTAMIC ACID"

( i x ) FEATURE:
        ( A ) NAME/KEY: Modified-site
        ( B ) LOCATION: 2
        ( D ) OTHER INFORMATION: /label=AA2
            / note= "AA2 is D-AA"

( i x ) FEATURE:
        ( A ) NAME/KEY: Modified-site
        ( B ) LOCATION: 3
        ( D ) OTHER INFORMATION: /label=AA3
            / note= "AA3 is D-AA"

( i x ) FEATURE:
        ( A ) NAME/KEY: Modified-site
        ( B ) LOCATION: 6
        ( D ) OTHER INFORMATION: /label=AA6
            / note= "AA6 is D-TRP"

( x i ) SEQUENCE DESCRIPTION: SEQ ID NO:5:

Xaa Phe Trp Ser Tyr Trp Leu Arg Pro Gly
1               5                   10

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site (B) LOCATION: 1
                (D) OTHER INFORMATION: /label=AA1-3
                    / note= "AA1 is ACETYL-BETA-2-NAPHTHYL-D-ALA, AA2 is
                    D-P-CHLORO- PHE, AA3 is BETA-3-PYRIDYL-D-ALA"

(ix) FEATURE:
                (A) NAME/KEY: Modified-site
                (B) LOCATION: 5
                (D) OTHER INFORMATION: /label=AA5-6
                    / note= "AA5-6 are each N-EPSILON-NICOTINOYL-LYS, AA6
                    is also D- LYS"

(ix) FEATURE:
                (A) NAME/KEY: Modified-site
                (B) LOCATION: 8
                (D) OTHER INFORMATION: /label=AA8
                    / note= "AA8 is N-EPSILON-ISOPROPYL-LYS"

(ix) FEATURE:
                (A) NAME/KEY: Modified-site
                (B) LOCATION: 10
                (D) OTHER INFORMATION: /label=AA10
                    / note= "AA10 is D-ALA"

(xi) SEQUENCE DESCRIPTION: SEQ ID NO:6:

Ala  Phe  Ala  Ser  Lys  Lys  Leu  Lys  Pro  Ala
    1                   5                        10

(2) INFORMATION FOR SEQ ID NO:7:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: protein (ix) FEATURE:
                (A) NAME/KEY: Modified-site
                (B) LOCATION: 1
                (D) OTHER INFORMATION: /label=AA1
                    / note= "AA1 is PYROGLUTAMIC ACID"

(ix) FEATURE:
                (A) NAME/KEY: Modified-site
                (B) LOCATION: 6
                (D) OTHER INFORMATION: /label=AA6
                    / note= "AA6 is D-LYS"

(xi) SEQUENCE DESCRIPTION: SEQ ID NO:7:

Xaa  His  Trp  Ser  Tyr  Lys  Leu  Arg  Pro  Gly
    1                   5                        10

(2) INFORMATION FOR SEQ ID NO:8:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: protein (ix) FEATURE:
                (A) NAME/KEY: Modified-site
                (B) LOCATION: 1
                (D) OTHER INFORMATION: /label=AA1
                    / note= "AA1 is PYROGLUTAMIC ACID"

(xi) SEQUENCE DESCRIPTION: SEQ ID NO:8:

Xaa  His  Trp  Ser  Tyr  Gly  Trp  Leu  Pro  Gly
    1                   5                        10

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /label=AA1
            / note= "AA1 is PYROGLUTAMIC ACID"

( x i ) SEQUENCE DESCRIPTION: SEQ ID NO:9:

Xaa  His  Trp  Ser  His  Gly  Leu  Asn  Pro  Gly
    1                      5                            10

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /label=AA1
            / note= "AA1 is PYROGLUTAMIC ACID"

( i x ) FEATURE:
        ( A ) NAME/KEY: Modified-site
        ( B ) LOCATION: 6
        ( D ) OTHER INFORMATION: /label=AA6
            / note= "AA6 is D-ARG"

( i x ) FEATURE:
        ( A ) NAME/KEY: Modified-site
        ( B ) LOCATION: 9
        ( D ) OTHER INFORMATION: /label=AA9
            / note= "AA9 is PRO-N-ETHYLAMIDE"

( x i ) SEQUENCE DESCRIPTION: SEQ ID NO:10:

Xaa  His  Trp  Ser  Tyr  Arg  Trp  Leu  Pro
    1                      5

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /label=AA1
            / note= "AA1 is PYROGLUTAMIC ACID"

( i x ) FEATURE:
        ( A ) NAME/KEY: Modified-site
        ( B ) LOCATION: 5..9
        ( D ) OTHER INFORMATION: /label=AA5-9
            / note= "AA5, AA7 & AA8 may be any D or L NAT. or
            NON-NAT. AA or derivative; AA8 esp. ASN, AA7 esp.
            LEU or TRP, AA5 esp. HIS, AA6 & AA9 are as in SEQ
            ID NO 3"

(xi) SEQUENCE DESCRIPTION: SEQ ID NO:11:

Xaa His Tyr Ser Xaa Xaa Xaa Xaa Xaa Gly
1               5                       10

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 1
        (D) OTHER INFORMATION: /label=AA1
            / note= "AA1 is PYROGLUTAMIC ACID"

(ix) FEATURE:
        (A) NAME/KEY: Modified-site
        (B) LOCATION: 5..9
        (D) OTHER INFORMATION: /label=AA5-9
            / note= "AA5, AA7 & AA8 may be any D- or L- NAT. or
            NON-NAT. AA or derivative; AA7 esp. LEU or TRP, AA8
            esp. ASN, AA5 esp. HIS; AA6 & AA9 are as in SEQ ID NO 4."

(xi) SEQUENCE DESCRIPTION: SEQ ID NO:12:

Xaa His Tyr Ser Xaa Xaa Xaa Xaa Xaa
1               5